(12) United States Patent
Boesen

(10) Patent No.: US 11,013,445 B2
(45) Date of Patent: May 25, 2021

(54) WIRELESS EARPIECE WITH TRANSCRANIAL STIMULATION

(71) Applicant: BRAGI GmbH, Munich (DE)

(72) Inventor: Peter Vincent Boesen, Munich (DE)

(73) Assignee: BRAGI GmbH, Munich (DE)

( * ) Notice: Subject to any disclaimer, the term of this patent is extended or adjusted under 35 U.S.C. 154(b) by 336 days.

(21) Appl. No.: 15/997,794

(22) Filed: Jun. 5, 2018

(65) Prior Publication Data

US 2018/0353095 A1 Dec. 13, 2018

Related U.S. Application Data

(60) Provisional application No. 62/516,868, filed on Jun. 8, 2017.

(51) Int. Cl.
*A61B 5/291* (2021.01)
*A61B 5/00* (2006.01)
(Continued)

(52) U.S. Cl.
CPC ............ *A61B 5/291* (2021.01); *A61B 5/0006* (2013.01); *A61B 5/0205* (2013.01); *A61B 5/4836* (2013.01); *A61B 5/6803* (2013.01); *G06F 3/012* (2013.01); *G06F 3/015* (2013.01); *G06F 3/017* (2013.01); *H04R 1/1016* (2013.01); *H04R 5/033* (2013.01); *A61B 5/165* (2013.01); *A61B 5/4088* (2013.01); *G06F 3/033* (2013.01); *H04M 1/6066* (2013.01); *H04R 2420/07* (2013.01); *H04R 2460/13* (2013.01)

(58) Field of Classification Search
CPC ........ A61N 2/00; A61N 2/002; A61N 2/0047; A61N 2/006; A61N 2/008; A61N 2/02; A61N 1/36014; A61N 1/36025; A61N 1/3606; A61N 1/36031; A61N 1/36034; A61B 5/0478
See application file for complete search history.

(56) References Cited

U.S. PATENT DOCUMENTS 2,325,590 A 8/1943 Carlisle et al.
2,430,229 A 11/1947 Kelsey
(Continued)

FOREIGN PATENT DOCUMENTS

CN 204244472 U 4/2015
CN 104683519 A 6/2015
(Continued)

OTHER PUBLICATIONS

Akkermans, "Acoustic Ear Recognition for Person Identification", Automatic Identification Advanced Technologies, 2005 pp. 219-223.
(Continued)

*Primary Examiner* — Carrie R Dorna
(74) *Attorney, Agent, or Firm* — Goodhue, Coleman & Owens, P.C.

(57) ABSTRACT

A wireless earpiece includes a wireless earpiece housing, a processor, and a transceiver configured to produce electromagnetic pulses capable of reaching a brain of a user. A method of stimulating the brain of the user using the wireless earpiece includes receiving a request at the wireless earpiece and generating an electromagnetic pulse in response to the request.

18 Claims, 8 Drawing Sheets

(51) Int. Cl.
*H04R 1/10* (2006.01)
*G06F 3/01* (2006.01)
*H04R 5/033* (2006.01)
*A61B 5/0205* (2006.01)
*H04M 1/60* (2006.01)
*A61B 5/16* (2006.01)
*G06F 3/033* (2013.01)

(56) References Cited

U.S. PATENT DOCUMENTS

| | | |
|---|---|---|
| 3,047,089 A | 7/1962 | Zwislocki |
| D208,784 S | 10/1967 | Sanzone |
| 3,586,794 A | 6/1971 | Michaelis |
| 3,696,377 A | 10/1972 | Wall |
| 3,934,100 A | 1/1976 | Harada |
| 3,983,336 A | 9/1976 | Malek et al. |
| 4,069,400 A | 1/1978 | Johanson et al. |
| 4,150,262 A | 4/1979 | Ono |
| 4,334,315 A | 6/1982 | Ono et al. |
| D266,271 S | 9/1982 | Johanson et al. |
| 4,375,016 A | 2/1983 | Harada |
| 4,588,867 A | 5/1986 | Konomi |
| 4,617,429 A | 10/1986 | Bellafiore |
| 4,654,883 A | 3/1987 | Iwata |
| 4,682,180 A | 7/1987 | Gans |
| 4,791,673 A | 12/1988 | Schreiber |
| 4,852,177 A | 7/1989 | Ambrose |
| 4,865,044 A | 9/1989 | Wallace et al. |
| 4,984,277 A | 1/1991 | Bisgaard et al. |
| 5,008,943 A | 4/1991 | Arndt et al. |
| 5,185,802 A | 2/1993 | Stanton |
| 5,191,602 A | 3/1993 | Regen et al. |
| 5,201,007 A | 4/1993 | Ward et al. |
| 5,201,008 A | 4/1993 | Arndt et al. |
| D340,286 S | 10/1993 | Seo |
| 5,280,524 A | 1/1994 | Norris |
| 5,295,193 A | 3/1994 | Ono |
| 5,298,692 A | 3/1994 | Ikeda et al. |
| 5,343,532 A | 8/1994 | Shugart |
| 5,347,584 A | 9/1994 | Narisawa |
| 5,363,444 A | 11/1994 | Norris |
| 5,444,786 A | 8/1995 | Raviv |
| D367,113 S | 2/1996 | Weeks |
| 5,497,339 A | 3/1996 | Bernard |
| 5,606,621 A | 2/1997 | Reiter et al. |
| 5,613,222 A | 3/1997 | Guenther |
| 5,654,530 A | 8/1997 | Sauer et al. |
| 5,692,059 A | 11/1997 | Kruger |
| 5,721,783 A | 2/1998 | Anderson |
| 5,748,743 A | 5/1998 | Weeks |
| 5,749,072 A | 5/1998 | Mazurkiewicz et al. |
| 5,771,438 A | 6/1998 | Palermo et al. |
| D397,796 S | 9/1998 | Yabe et al. |
| 5,802,167 A | 9/1998 | Hong |
| 5,844,996 A | 12/1998 | Enzmann et al. |
| D410,008 S | 5/1999 | Almqvist |
| 5,929,774 A | 7/1999 | Charlton |
| 5,933,506 A | 8/1999 | Aoki et al. |
| 5,949,896 A | 9/1999 | Nageno et al. |
| 5,987,146 A | 11/1999 | Pluvinage et al. |
| 6,021,207 A | 2/2000 | Puthuff et al. |
| 6,054,989 A | 4/2000 | Robertson et al. |
| 6,081,724 A | 6/2000 | Wilson |
| 6,084,526 A | 7/2000 | Blotky et al. |
| 6,094,492 A | 7/2000 | Boesen |
| 6,111,569 A | 8/2000 | Brusky et al. |
| 6,112,103 A | 8/2000 | Puthuff |
| 6,157,727 A | 12/2000 | Rueda |
| 6,167,039 A | 12/2000 | Karlsson et al. |
| 6,181,801 B1 | 1/2001 | Puthuff et al. |
| 6,185,152 B1 | 2/2001 | Shen |
| 6,208,372 B1 | 3/2001 | Barraclough |
| 6,230,029 B1 | 5/2001 | Yegiazaryan et al. |
| 6,275,789 B1 | 8/2001 | Moser et al. |
| 6,339,754 B1 | 1/2002 | Flanagan et al. |
| D455,835 S | 4/2002 | Anderson et al. |
| 6,408,081 B1 | 6/2002 | Boesen |
| 6,424,820 B1 | 7/2002 | Burdick et al. |
| D464,039 S | 10/2002 | Boesen |
| 6,470,893 B1 | 10/2002 | Boesen |
| D468,299 S | 1/2003 | Boesen |
| D468,300 S | 1/2003 | Boesen |
| 6,542,721 B2 | 4/2003 | Boesen |
| 6,560,468 B1 | 5/2003 | Boesen |
| 6,563,301 B2 | 5/2003 | Gventer |
| 6,654,721 B2 | 11/2003 | Handelman |
| 6,664,713 B2 | 12/2003 | Boesen |
| 6,690,807 B1 | 2/2004 | Meyer |
| 6,694,180 B1 | 2/2004 | Boesen |
| 6,718,043 B1 | 4/2004 | Boesen |
| 6,738,485 B1 | 5/2004 | Boesen |
| 6,748,095 B1 | 6/2004 | Goss |
| 6,754,358 B1 | 6/2004 | Boesen et al. |
| 6,784,873 B1 | 8/2004 | Boesen et al. |
| 6,823,195 B1 | 11/2004 | Boesen |
| 6,852,084 B1 | 2/2005 | Boesen |
| 6,879,698 B2 | 4/2005 | Boesen |
| 6,892,082 B2 | 5/2005 | Boesen |
| 6,920,229 B2 | 7/2005 | Boesen |
| 6,952,483 B2 | 10/2005 | Boesen et al. |
| 6,987,986 B2 | 1/2006 | Boesen |
| 7,010,137 B1 | 3/2006 | Leedom et al. |
| 7,113,611 B2 | 9/2006 | Leedom et al. |
| D532,520 S | 11/2006 | Kampmeier et al. |
| 7,136,282 B1 | 11/2006 | Rebeske |
| 7,203,331 B2 | 4/2007 | Boesen |
| 7,209,569 B2 | 4/2007 | Boesen |
| 7,215,790 B2 | 5/2007 | Boesen et al. |
| D549,222 S | 8/2007 | Huang |
| D554,756 S | 11/2007 | Sjursen et al. |
| 7,403,629 B1 | 7/2008 | Aceti et al. |
| D579,006 S | 10/2008 | Kim et al. |
| 7,463,902 B2 | 12/2008 | Boesen |
| 7,508,411 B2 | 3/2009 | Boesen |
| 7,532,901 B1 | 5/2009 | LaFranchise et al. |
| D601,134 S | 9/2009 | Elabidi et al. |
| 7,825,626 B2 | 11/2010 | Kozisek |
| 7,859,469 B1 | 12/2010 | Rosener et al. |
| 7,965,855 B1 | 6/2011 | Ham |
| 7,979,035 B2 | 7/2011 | Griffin et al. |
| 7,983,628 B2 | 7/2011 | Boesen |
| D647,491 S | 10/2011 | Chen et al. |
| 8,095,188 B2 | 1/2012 | Shi |
| 8,108,143 B1 | 1/2012 | Tester |
| 8,140,357 B1 | 3/2012 | Boesen |
| 8,204,786 B2 | 6/2012 | LeBoeuf et al. |
| D666,581 S | 9/2012 | Perez |
| 8,300,864 B2 | 10/2012 | Müenborn et al. |
| 8,406,448 B2 | 3/2013 | Lin et al. |
| 8,430,817 B1 | 4/2013 | Al-Ali et al. |
| 8,436,780 B2 | 5/2013 | Schantz et al. |
| D687,021 S | 7/2013 | Yuen |
| 8,679,012 B1 | 3/2014 | Kayyali |
| 8,719,877 B2 | 5/2014 | VonDoenhoff et al. |
| 8,774,434 B2 | 7/2014 | Zhao et al. |
| 8,831,266 B1 | 9/2014 | Huang |
| 8,891,800 B1 | 11/2014 | Shaffer |
| 8,994,498 B2 | 3/2015 | Agrafioti et al. |
| D728,107 S | 4/2015 | Martin et al. |
| 9,013,145 B2 | 4/2015 | Castillo et al. |
| 9,037,125 B1 | 5/2015 | Kadous |
| D733,103 S | 6/2015 | Jeong et al. |
| 9,081,944 B2 | 7/2015 | Camacho et al. |
| 9,461,403 B2 | 10/2016 | Gao et al. |
| 9,510,159 B1 | 11/2016 | Cuddihy et al. |
| D773,439 S | 12/2016 | Walker |
| D775,158 S | 12/2016 | Dong et al. |
| D777,710 S | 1/2017 | Palmborg et al. |
| 9,544,689 B2 | 1/2017 | Fisher et al. |
| D788,079 S | 5/2017 | Son et al. |
| 9,684,778 B2 | 6/2017 | Tharappel et al. |
| 9,711,062 B2 | 7/2017 | Ellis et al. |
| 9,729,979 B2 | 8/2017 | Özden |
| 9,755,704 B2 | 9/2017 | Hviid et al. |

(56) References Cited

U.S. PATENT DOCUMENTS

| | | |
|---|---|---|
| 9,767,709 B2 | 9/2017 | Ellis |
| 9,813,826 B2 | 11/2017 | Hviid et al. |
| 9,848,257 B2 | 12/2017 | Ambrose et al. |
| 9,949,008 B2 | 4/2018 | Hviid et al. |
| 2001/0005197 A1 | 6/2001 | Mishra et al. |
| 2001/0027121 A1 | 10/2001 | Boesen |
| 2001/0043707 A1 | 11/2001 | Leedom |
| 2001/0056350 A1 | 12/2001 | Calderone et al. |
| 2002/0002413 A1 | 1/2002 | Tokue |
| 2002/0007510 A1 | 1/2002 | Mann |
| 2002/0010590 A1 | 1/2002 | Lee |
| 2002/0030637 A1 | 3/2002 | Mann |
| 2002/0046035 A1 | 4/2002 | Kitahara et al. |
| 2002/0057810 A1 | 5/2002 | Boesen |
| 2002/0076073 A1 | 6/2002 | Taenzer et al. |
| 2002/0118852 A1 | 8/2002 | Boesen |
| 2003/0002705 A1 | 1/2003 | Boesen |
| 2003/0065504 A1 | 4/2003 | Kraemer et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2004/0070564 A1 | 4/2004 | Dawson et al. |
| 2004/0102931 A1 | 5/2004 | Ellis et al. |
| 2004/0160511 A1 | 8/2004 | Boesen |
| 2005/0017842 A1 | 1/2005 | Dematteo |
| 2005/0043056 A1 | 2/2005 | Boesen |
| 2005/0094839 A1 | 5/2005 | Gwee |
| 2005/0125320 A1 | 6/2005 | Boesen |
| 2005/0148883 A1 | 7/2005 | Boesen |
| 2005/0165663 A1 | 7/2005 | Razumov |
| 2005/0196009 A1 | 9/2005 | Boesen |
| 2005/0197063 A1 | 9/2005 | White |
| 2005/0212911 A1 | 9/2005 | Marvit et al. |
| 2005/0251455 A1 | 11/2005 | Boesen |
| 2005/0266876 A1 | 12/2005 | Boesen |
| 2006/0029246 A1 | 2/2006 | Boesen |
| 2006/0073787 A1 | 4/2006 | Lair et al. |
| 2006/0074671 A1 | 4/2006 | Farmaner et al. |
| 2006/0074808 A1 | 4/2006 | Boesen |
| 2006/0166715 A1 | 7/2006 | Engelen et al. |
| 2006/0166716 A1 | 7/2006 | Seshadri et al. |
| 2006/0220915 A1 | 10/2006 | Bauer |
| 2006/0258412 A1 | 11/2006 | Liu |
| 2007/0102009 A1 | 5/2007 | Wong et al. |
| 2007/0239225 A1 | 10/2007 | Saringer |
| 2007/0269785 A1 | 11/2007 | Yamanoi |
| 2008/0076972 A1 | 3/2008 | Dorogusker et al. |
| 2008/0090622 A1 | 4/2008 | Kim et al. |
| 2008/0102424 A1 | 5/2008 | Holljes |
| 2008/0146890 A1 | 6/2008 | LeBoeuf et al. |
| 2008/0187163 A1 | 8/2008 | Goldstein et al. |
| 2008/0215239 A1 | 9/2008 | Lee |
| 2008/0253583 A1 | 10/2008 | Goldstein et al. |
| 2008/0254780 A1 | 10/2008 | Kuhl et al. |
| 2008/0255430 A1 | 10/2008 | Alexandersson et al. |
| 2008/0298606 A1 | 12/2008 | Johnson et al. |
| 2009/0003620 A1 | 1/2009 | McKillop et al. |
| 2009/0008275 A1 | 1/2009 | Ferrari et al. |
| 2009/0017881 A1 | 1/2009 | Madrigal |
| 2009/0041313 A1 | 2/2009 | Brown |
| 2009/0073070 A1 | 3/2009 | Rofougaran |
| 2009/0097689 A1 | 4/2009 | Prest et al. |
| 2009/0105548 A1 | 4/2009 | Bart |
| 2009/0154739 A1 | 6/2009 | Zellner |
| 2009/0191920 A1 | 7/2009 | Regen et al. |
| 2009/0226017 A1 | 9/2009 | Abolfathi et al. |
| 2009/0240947 A1 | 9/2009 | Goyal et al. |
| 2009/0245559 A1 | 10/2009 | Boltyenkov et al. |
| 2009/0247894 A1* | 10/2009 | Causevic .............. A61B 5/7225 600/544 |
| 2009/0261114 A1 | 10/2009 | McGuire et al. |
| 2009/0296968 A1 | 12/2009 | Wu et al. |
| 2009/0303073 A1 | 12/2009 | Gilling et al. |
| 2009/0304210 A1 | 12/2009 | Weisman |
| 2010/0033313 A1 | 2/2010 | Keady et al. |
| 2010/0075631 A1 | 3/2010 | Black et al. |
| 2010/0166206 A1 | 7/2010 | Macours |
| 2010/0203831 A1 | 8/2010 | Muth |
| 2010/0210212 A1 | 8/2010 | Sato |
| 2010/0290636 A1 | 11/2010 | Mao et al. |
| 2010/0320961 A1 | 12/2010 | Castillo et al. |
| 2011/0018731 A1 | 1/2011 | Linsky et al. |
| 2011/0103609 A1 | 5/2011 | Pelland et al. |
| 2011/0137141 A1 | 6/2011 | Razoumov et al. |
| 2011/0140844 A1 | 6/2011 | McGuire et al. |
| 2011/0239497 A1 | 10/2011 | McGuire et al. |
| 2011/0286615 A1 | 11/2011 | Olodort et al. |
| 2011/0293105 A1 | 12/2011 | Ade et al. |
| 2012/0057740 A1 | 3/2012 | Rosal |
| 2012/0155670 A1 | 6/2012 | Rutschman |
| 2012/0159617 A1 | 6/2012 | Wu et al. |
| 2012/0163626 A1 | 6/2012 | Booij et al. |
| 2012/0197737 A1 | 8/2012 | LeBoeuf et al. |
| 2012/0235883 A1 | 9/2012 | Border et al. |
| 2012/0309453 A1 | 12/2012 | Maguire |
| 2013/0106454 A1 | 5/2013 | Liu et al. |
| 2013/0154826 A1 | 6/2013 | Ratajczyk |
| 2013/0178967 A1 | 7/2013 | Mentz |
| 2013/0200999 A1 | 8/2013 | Spodak et al. |
| 2013/0204617 A1 | 8/2013 | Kuo et al. |
| 2013/0293494 A1 | 11/2013 | Reshef |
| 2013/0316642 A1 | 11/2013 | Newham |
| 2013/0346168 A1 | 12/2013 | Zhou et al. |
| 2014/0004912 A1 | 1/2014 | Rajakarunanayake |
| 2014/0014697 A1 | 1/2014 | Schmierer et al. |
| 2014/0020089 A1 | 1/2014 | Perini, II |
| 2014/0072136 A1 | 3/2014 | Tenenbaum et al. |
| 2014/0072146 A1 | 3/2014 | Itkin et al. |
| 2014/0073429 A1 | 3/2014 | Meneses et al. |
| 2014/0079257 A1 | 3/2014 | Ruwe et al. |
| 2014/0106677 A1 | 4/2014 | Altman |
| 2014/0122116 A1 | 5/2014 | Smythe |
| 2014/0146973 A1 | 5/2014 | Liu et al. |
| 2014/0153768 A1 | 6/2014 | Hagen et al. |
| 2014/0163771 A1 | 6/2014 | Demeniuk |
| 2014/0185828 A1 | 7/2014 | Helbling |
| 2014/0219467 A1 | 8/2014 | Kurtz |
| 2014/0222462 A1 | 8/2014 | Shakil et al. |
| 2014/0235169 A1 | 8/2014 | Parkinson et al. |
| 2014/0270227 A1 | 9/2014 | Swanson |
| 2014/0270271 A1 | 9/2014 | Dehe et al. |
| 2014/0276227 A1 | 9/2014 | Pérez |
| 2014/0310595 A1 | 10/2014 | Acharya et al. |
| 2014/0321682 A1 | 10/2014 | Kofod-Hansen et al. |
| 2014/0335908 A1 | 11/2014 | Krisch et al. |
| 2014/0348367 A1 | 11/2014 | Vavrus et al. |
| 2015/0028996 A1 | 1/2015 | Agrafioti et al. |
| 2015/0035643 A1 | 2/2015 | Kursun |
| 2015/0036835 A1 | 2/2015 | Chen |
| 2015/0056584 A1 | 2/2015 | Boulware et al. |
| 2015/0110587 A1 | 4/2015 | Hori |
| 2015/0148989 A1 | 5/2015 | Cooper et al. |
| 2015/0181356 A1 | 6/2015 | Krystek et al. |
| 2015/0230022 A1 | 8/2015 | Sakai et al. |
| 2015/0245127 A1 | 8/2015 | Shaffer |
| 2015/0256949 A1 | 9/2015 | Vanpoucke et al. |
| 2015/0264472 A1 | 9/2015 | Aase |
| 2015/0264501 A1 | 9/2015 | Hu et al. |
| 2015/0317565 A1 | 11/2015 | Li et al. |
| 2015/0358751 A1 | 12/2015 | Deng et al. |
| 2015/0359436 A1 | 12/2015 | Shim et al. |
| 2015/0364058 A1 | 12/2015 | Lagree et al. |
| 2015/0373467 A1 | 12/2015 | Gelter |
| 2015/0373474 A1 | 12/2015 | Kraft et al. |
| 2015/0379251 A1 | 12/2015 | Komaki |
| 2016/0033280 A1 | 2/2016 | Moore et al. |
| 2016/0034249 A1 | 2/2016 | Lee et al. |
| 2016/0071526 A1 | 3/2016 | Wingate et al. |
| 2016/0072558 A1 | 3/2016 | Hirsch et al. |
| 2016/0073189 A1 | 3/2016 | Linden et al. |
| 2016/0094550 A1 | 3/2016 | Bradley et al. |
| 2016/0100262 A1 | 4/2016 | Inagaki |

(56) References Cited

U.S. PATENT DOCUMENTS

| | | |
|---|---|---|
| 2016/0119737 A1 | 4/2016 | Mehnert et al. |
| 2016/0124707 A1 | 5/2016 | Ermilov et al. |
| 2016/0125892 A1 | 5/2016 | Bowen et al. |
| 2016/0140870 A1 | 5/2016 | Connor |
| 2016/0142818 A1 | 5/2016 | Park |
| 2016/0162259 A1 | 6/2016 | Zhao et al. |
| 2016/0209691 A1 | 7/2016 | Yang et al. |
| 2016/0253994 A1 | 9/2016 | Panchapagesan et al. |
| 2016/0279435 A1* | 9/2016 | Hyde ............... A61N 1/36036 |
| 2016/0324478 A1 | 11/2016 | Goldstein |
| 2016/0353196 A1 | 12/2016 | Baker et al. |
| 2016/0360350 A1 | 12/2016 | Watson et al. |
| 2017/0021257 A1 | 1/2017 | Gilbert et al. |
| 2017/0046503 A1 | 2/2017 | Cho et al. |
| 2017/0059152 A1 | 3/2017 | Hirsch et al. |
| 2017/0060262 A1 | 3/2017 | Hviid et al. |
| 2017/0060269 A1 | 3/2017 | Förstner et al. |
| 2017/0061751 A1 | 3/2017 | Loermann et al. |
| 2017/0061817 A1 | 3/2017 | Mettler May |
| 2017/0062913 A1 | 3/2017 | Hirsch et al. |
| 2017/0064426 A1 | 3/2017 | Hviid |
| 2017/0064428 A1 | 3/2017 | Hirsch |
| 2017/0064432 A1 | 3/2017 | Hviid et al. |
| 2017/0064437 A1 | 3/2017 | Hviid et al. |
| 2017/0078780 A1 | 3/2017 | Qian et al. |
| 2017/0078785 A1 | 3/2017 | Qian et al. |
| 2017/0100277 A1 | 4/2017 | Ke |
| 2017/0108918 A1 | 4/2017 | Boesen |
| 2017/0109131 A1 | 4/2017 | Boesen |
| 2017/0110124 A1 | 4/2017 | Boesen et al. |
| 2017/0110899 A1 | 4/2017 | Boesen |
| 2017/0111723 A1 | 4/2017 | Boesen |
| 2017/0111725 A1 | 4/2017 | Boesen et al. |
| 2017/0111726 A1 | 4/2017 | Martin et al. |
| 2017/0111740 A1 | 4/2017 | Hviid et al. |
| 2017/0127168 A1 | 5/2017 | Briggs et al. |
| 2017/0131094 A1 | 5/2017 | Kulik |
| 2017/0142511 A1 | 5/2017 | Dennis |
| 2017/0146801 A1 | 5/2017 | Stempora |
| 2017/0150920 A1 | 6/2017 | Chang et al. |
| 2017/0151085 A1 | 6/2017 | Chang et al. |
| 2017/0151447 A1 | 6/2017 | Boesen |
| 2017/0151668 A1 | 6/2017 | Boesen |
| 2017/0151918 A1 | 6/2017 | Boesen |
| 2017/0151930 A1 | 6/2017 | Boesen |
| 2017/0151957 A1 | 6/2017 | Boesen |
| 2017/0151959 A1 | 6/2017 | Boesen |
| 2017/0153114 A1 | 6/2017 | Boesen |
| 2017/0153636 A1 | 6/2017 | Boesen |
| 2017/0154532 A1 | 6/2017 | Boesen |
| 2017/0155985 A1 | 6/2017 | Boesen |
| 2017/0155992 A1 | 6/2017 | Perianu et al. |
| 2017/0155993 A1 | 6/2017 | Boesen |
| 2017/0155997 A1 | 6/2017 | Boesen |
| 2017/0155998 A1 | 6/2017 | Boesen |
| 2017/0156000 A1 | 6/2017 | Boesen |
| 2017/0164890 A1 | 6/2017 | Leip et al. |
| 2017/0178631 A1 | 6/2017 | Boesen |
| 2017/0180842 A1 | 6/2017 | Boesen |
| 2017/0180843 A1 | 6/2017 | Perianu et al. |
| 2017/0180897 A1 | 6/2017 | Perianu |
| 2017/0188127 A1 | 6/2017 | Perianu et al. |
| 2017/0188132 A1 | 6/2017 | Hirsch et al. |
| 2017/0193978 A1 | 7/2017 | Goldman |
| 2017/0195829 A1 | 7/2017 | Belverato et al. |
| 2017/0208393 A1 | 7/2017 | Boesen |
| 2017/0214987 A1 | 7/2017 | Boesen |
| 2017/0215016 A1 | 7/2017 | Dohmen et al. |
| 2017/0230752 A1 | 8/2017 | Dohmen et al. |
| 2017/0251933 A1 | 9/2017 | Braun et al. |
| 2017/0257698 A1 | 9/2017 | Boesen et al. |
| 2017/0258329 A1 | 9/2017 | Marsh |
| 2017/0263236 A1 | 9/2017 | Boesen et al. |
| 2017/0263376 A1 | 9/2017 | Verschueren et al. |
| 2017/0266494 A1 | 9/2017 | Crankson et al. |
| 2017/0273622 A1 | 9/2017 | Boesen |
| 2017/0280257 A1 | 9/2017 | Gordon et al. |
| 2017/0301337 A1 | 10/2017 | Golani et al. |
| 2017/0361093 A1* | 12/2017 | Yoo ............... A61N 2/02 |
| 2017/0361213 A1 | 12/2017 | Goslin et al. |
| 2017/0366233 A1 | 12/2017 | Hviid et al. |
| 2018/0007994 A1 | 1/2018 | Boesen et al. |
| 2018/0008194 A1 | 1/2018 | Boesen |
| 2018/0008198 A1 | 1/2018 | Kingscott |
| 2018/0009447 A1 | 1/2018 | Boesen et al. |
| 2018/0011006 A1 | 1/2018 | Kingscott |
| 2018/0011682 A1 | 1/2018 | Milevski et al. |
| 2018/0011994 A1 | 1/2018 | Boesen |
| 2018/0012228 A1 | 1/2018 | Milevski et al. |
| 2018/0013195 A1 | 1/2018 | Hviid et al. |
| 2018/0014102 A1 | 1/2018 | Hirsch et al. |
| 2018/0014103 A1 | 1/2018 | Martin et al. |
| 2018/0014104 A1 | 1/2018 | Boesen et al. |
| 2018/0014107 A1 | 1/2018 | Razouane et al. |
| 2018/0014108 A1 | 1/2018 | Dragicevic et al. |
| 2018/0014109 A1 | 1/2018 | Boesen |
| 2018/0014113 A1 | 1/2018 | Boesen |
| 2018/0014140 A1 | 1/2018 | Milevski et al. |
| 2018/0014436 A1 | 1/2018 | Milevski |
| 2018/0034951 A1 | 2/2018 | Boesen |
| 2018/0040093 A1 | 2/2018 | Boesen |
| 2018/0042501 A1 | 2/2018 | Adi et al. |

FOREIGN PATENT DOCUMENTS

| | | |
|---|---|---|
| EP | 1469659 A1 | 10/2004 |
| EP | 1017252 A3 | 5/2006 |
| EP | 2903186 A1 | 8/2015 |
| GB | 2074817 | 4/1981 |
| GB | 2508226 A | 5/2014 |
| JP | 06292195 | 10/1998 |
| WO | 2008103925 A1 | 8/2008 |
| WO | 2008113053 A1 | 9/2008 |
| WO | 2007034371 A3 | 11/2008 |
| WO | 2011001433 A2 | 1/2011 |
| WO | 2012071127 A1 | 5/2012 |
| WO | 2013134956 A1 | 9/2013 |
| WO | 2014046602 A1 | 3/2014 |
| WO | 2014043179 A3 | 7/2014 |
| WO | 2015061633 A2 | 4/2015 |
| WO | 2015110577 A1 | 7/2015 |
| WO | 2015110587 A1 | 7/2015 |
| WO | 2016032990 A1 | 3/2016 |
| WO | 2016187869 A1 | 12/2016 |

OTHER PUBLICATIONS

Alzahrani et al: "A Multi-Channel Opto-Electronic Sensor to Accurately Monitor Heart Rate against Motion Artefact during Exercise", Sensors, vol. 15, No. 10, Oct. 12, 2015, pp. 25681-25702, XP055334602, DOI: 10.3390/s151025681 the whole document.

Announcing the $3,333,333 Stretch Goal (Feb. 24, 2014).

Ben Coxworth: "Graphene-based ink could enable low-cost, foldable electronics", "Journal of Physical Chemistry Letters", Northwestern University, (May 22, 2013).

Blain: "World's first graphene speaker already superior to Sennheiser MX400", htt://www.gizmag.com/graphene-speaker-beats-sennheiser-mx400/31660, (Apr. 15, 2014).

BMW, "BMW introduces BMW Connected—The personalized digital assistant", "http://bmwblog.com/2016/01/05/bmw-ntroduces-bmw-connected-the-personalized-digital-assistant", (Jan. 5, 2016).

BRAGI Is on Facebook (2014).

BRAGI Update—Arrival of Prototype Chassis Parts—More People—Awesomeness (May 13, 2014).

BRAGI Update—Chinese New Year, Design Verification, Charging Case, More People, Timeline(Mar. 6, 2015).

BRAGI Update—First Sleeves From Prototype Tool—Software Development Kit (Jun. 12, 2014).

BRAGI Update—Let's Get Ready to Rumble, A Lot to Be Done Over Christmas (Dec. 22, 2014).

(56) References Cited

OTHER PUBLICATIONS

BRAGI Update—Memories From April—Update on Progress (Sep. 16, 2014).
BRAGI Update—Memories from May—Update on Progress—Sweet (Oct. 13, 2014).
BRAGI Update—Memories From One Month Before Kickstarter—Update on Progress (Jul. 10, 2014).
BRAGI Update—Memories From the First Month of Kickstarter—Update on Progress (Aug. 1, 2014).
BRAGI Update—Memories From the Second Month of Kickstarter—Update on Progress (Aug. 22, 2014).
BRAGI Update—New People @BRAGI—Prototypes (Jun. 26, 2014).
BRAGI Update—Office Tour, Tour to China, Tour to CES (Dec. 11, 2014).
BRAGI Update—Status on Wireless, Bits and Pieces, Testing—Oh Yeah, Timeline(Apr. 24, 2015).
BRAGI Update—The App Preview, The Charger, The SDK, BRAGI Funding and Chinese New Year (Feb. 11, 2015).
BRAGI Update—What We Did Over Christmas, Las Vegas & CES (Jan. 19, 2014).
BRAGI Update—Years of Development, Moments of Utter Joy and Finishing What We Started(Jun. 15, 2015).
BRAGI Update—Alpha 5 and Back to China, Backer Day, On Track(May 16, 2015).
BRAGI Update—Beta2 Production and Factory Line(Aug. 20, 2015).
BRAGI Update—Certifications, Production, Ramping Up (Nov. 13, 2015).
BRAGI Update—Developer Units Shipping and Status(Oct. 5, 2015).
BRAGI Update—Developer Units Started Shipping and Status (Oct. 19, 2015).
BRAGI Update—Developer Units, Investment, Story and Status(Nov. 2, 2015).
BRAGI Update—Getting Close(Aug. 6, 2015).
BRAGI Update—On Track, Design Verification, How It Works and What's Next(Jul. 15, 2015).
BRAGI Update—On Track, On Track and Gems Overview (Jun. 24, 2015).
BRAGI Update—Status on Wireless, Supply, Timeline and Open House@BRAGI(Apr. 1, 2015).
BRAGI Update—Unpacking Video, Reviews on Audio Perform and Boy Are We Getting Close(Sep. 10, 2015).
Healthcare Risk Management Review, "Nuance updates computer-assisted physician documentation solution" (Oct. 20, 2016).
Hoffman, "How to Use Android Beam to Wirelessly Transfer Content Between Devices", (Feb. 22, 2013).
Hoyt et. al., "Lessons Learned from Implementation of Voice Recognition for Documentation in the Military Electronic Health Record System", The American Health Information Management Association (2017).
Hyundai Motor America, "Hyundai Motor Company Introduces a Health + Mobility Concept for Wellness in Mobility", Fountain Valley, California (2017).
International Search Report & Written Opinion, PCT/EP16/70245 (dated Nov. 16, 2016).
International Search Report & Written Opinion, PCT/EP2016/070231 (dated Nov. 18, 2016).
International Search Report & Written Opinion, PCT/EP2016/070247 (dated Nov. 18, 2016).
International Search Report & Written Opinion, PCT/EP2016/07216 (dated Oct. 18, 2016).
International Search Report and Written Opinion, PCT/EP2016/070228 (dated Jan. 9, 2017).
Jain A et al: "Score normalization in multimodal biometric systems", Pattern Recognition, Elsevier, GB, vol. 38, No. 12, Dec. 31, 2005, pp. 2270-2285, XP027610849, ISSN: 0031-3203.
Last Push Before the Kickstarter Campaign Ends on Monday 4pm CET (Mar. 28, 2014).
Lovejoy: "Touch Id built into iPhone display one step closer as third-party company announces new tech", "http://9to5mac.com/2015/07/21/virtualhomebutton/" (Jul. 21, 2015).
Nemanja Paunovic et al, "A methodology for testing complex professional electronic systems", Serbian Journal of Electrical Engineering, vol. 9, No. 1, Feb. 1, 2012, pp. 71-80, XPO55317584, Yu.
Nigel Whitfield: "Fake tape detectors, 'from the stands' footie and UGH? Internet of Things in my set-top box"; http://www.theregisterco.uk/2014/09/24/ibc_round_up_object_audio_dlna_iot/ (Sep. 24, 2014).
Nuance, "ING Netherlands Launches Voice Biometrics Payment System in the Mobile Banking App Powered by Nuance", "https://www.nuance.com/about-us/newsroom/press-releases/ing-netherlands-launches-nuance-voice-biometirics.html", 4 pages (Jul. 28, 2015).
Staab, Wayne J., et al., "A One-Size Disposable Hearing Aid is Introduced", The Hearing Journal 53(4):36-41) Apr. 2000.
Stretchgoa—Its Your Dash (Feb. 14, 2014).
Stretchgoal—The Carrying Case for The Dash (Feb. 12, 2014).
Stretchgoal—Windows Phone Support (Feb. 17, 2014).
The Dash + The Charging Case & The BRAGI News (Feb. 21, 2014).
The Dash—A Word From Our Software, Mechanical and Acoustics Team + An Update (Mar. 11, 2014).
Update From BRAGI—$3,000,000—Yipee (Mar. 22, 2014).
Weisiger; "Conjugated Hyperbilirubinemia", Jan. 5, 2016.
Wertzner et al., "Analysis of fundamental frequency, jitter, shimmer and vocal intensity in children with phonological disorders", V. 71, n5, 582-588, Sep./Oct. 2005; Brazilian Journal of Othrhinolaryngology.
Wikipedia, "Gamebook", https://en.wikipedia.org/wiki/Gamebook, Sep. 3, 2017, 5 pages.
Wikipedia, "Kinect", "https://en.wikipedia.org/wiki/Kinect", 18 pages, (Sep. 9, 2017).
Wikipedia, "Wii Balance Board", "https://en.wikipedia.org/wiki/Wii_Balance_Board", 3 pages, (Jul. 20, 2017).

* cited by examiner

WIRELESS EARPIECE WITH TRANSCRANIAL STIMULATION

PRIORITY STATEMENT

This application claims priority to 62/516,868 filed on Jun. 8, 2017, hereby incorporated by reference in its entirety.

FIELD OF THE INVENTION

The illustrative aspects of the present invention relate to wearable devices. More particularly, but not exclusively, the illustrative aspects of the present invention relate to wireless earpieces.

BACKGROUND

Transcranial stimulation is a medical technique used to evaluate motor function or brain damage resulting from a stroke, motor neuron disease, amyotrophic lateral sclerosis, or other neurodegenerative disease or disorder. Transcranial stimulation has also shown potential efficacy in helping people with depression or neuropathic-related pain. Recently, transcranial stimulation has shown promise in improving memory recall. Transcranial stimulation may be achieved by stimulating a user's brain with electromagnetic pulses. Therefore, what is needed is a wearable device capable of providing transcranial stimulation as needed for treatment.

SUMMARY

Therefore, it is a primary object, feature, or advantage of the illustrative aspects of the present invention to improve over the state of the art.

It is a further object, feature, or advantage of the illustrative aspects of the present invention to generate electromagnetic pulses with a transceiver to stimulate a user's brain.

It is a still further object, feature, or advantage of the illustrative aspects of the present invention to use electromagnetic pulses to stimulate a user's memory.

Another object, feature, or advantage is to use magnetic coils to generate electromagnetic pulses capable of stimulating a user's brain.

Yet another object, feature, or advantage is to use magnetic coils of different compositions and geometries to generate electromagnetic pulses capable of stimulating a user's brain.

Yet another object, feature, or advantage is to use electromagnetic pulses generated by magnetic coils to stimulate a user's memory.

Yet another object, feature, or advantage is to sense electrical activity from the user's brain using a plurality of EEG sensors.

Yet another object, feature, or advantage is to sense electrical activity from the user's brain using a plurality of EEG sensors resulting from electromagnetic pulses generated by a transceiver or one or more magnetic coils of a wireless earpiece.

Yet another object, feature, or advantage is to use the electrical activity from a user's brain produced in response to an electromagnetic pulse from the wireless earpiece to make a neurological or medical diagnosis.

One or more of these and/or other objects, features, or advantages of the illustrative aspects of the present invention will become apparent from the specification and claims that follow. No single aspect of the present invention need provide each and every object, feature, or advantage. Different aspects may have different objects, features, or advantages. Therefore, the illustrative aspects of the present invention are not to be limited to or by any object, feature, or advantage stated herein.

In one aspect of the present invention, a wireless earpiece includes a wireless earpiece housing, a processor disposed within the earpiece housing, and a transceiver operatively connected to the earpiece housing and the processor. Furthermore, the transceiver is configured to produce electromagnetic pulses capable of reaching a user's brain.

One or more of the following features may be included. A memory may be operatively connected to the earpiece housing and the processor. A magnetic coil may be operatively connected to the earpiece housing and the processor. A plurality of EEG sensors may be operatively connected to the earpiece housing and the processor. A differential amplifier may be operatively connected to the earpiece housing, the processor, and each EEG sensor. A neurological program may be stored on the memory. The neurological program may comprise a set of instructions for diagnosing a user's memory. The wireless earpiece may be a headset.

In another aspect of the present invention, a set of wireless earpieces includes a wireless earpiece housing, a processor disposed within each earpiece housing, a transceiver disposed within each earpiece housing and operatively connected to the processor in the earpiece housing in which the transceiver resides, a magnetic coil mounted to each earpiece housing and operatively connected to the processor in the earpiece housing in which the magnetic coil is mounted to, and a number of EEG sensors mounted to each earpiece housing and operatively connected to the processor in the earpiece housing in which each of the EEG sensors is mounted. Furthermore, the transceiver and the magnetic coil are configured to produce electromagnetic pulses capable of reaching a brain of the user and each of the EEG sensors is configured to sense electrical signals from the user's brain produced in response to the electromagnetic pulses.

One or more of the following features may be included. The set of wireless earpieces may comprise a left wireless earpiece and a right wireless earpiece. Each wireless earpiece may further comprise a memory disposed within each earpiece housing and operatively connected to the processor in the earpiece housing in which the memory resides, wherein each memory may include a neurological program stored within. A differential amplifier may be disposed within each earpiece housing and operatively connected to the processor in the earpiece housing in which the differential amplifier resides, wherein each differential amplifier may be configured to remove common mode gains from the electrical signals from the user's brain. Each differential amplifier may be further configured to filter noise from one or more electronic objects from the electrical signals from the user's brain.

In another aspect of the present invention, a method of stimulating a user's brain using a wireless earpiece includes receiving a request to stimulate the user's brain at the wireless earpiece and generating an electromagnetic pulse capable of reaching the user's brain by the earpiece in response to the request.

One or more of the following features may be included. The electromagnetic pulse may be generated by a NFMI transceiver. A party may be prompted for additional information if the request is a request to use a neurological program. The party may be a user or a third party. One or more electrical signals may be received from the user's brain in response to the electromagnetic pulses. Results related to the electrical signals from the user's brain may be provided. The results may comprise neurological analysis.

According to another aspect, a wireless earpiece for stimulating a user's brain includes a wireless earpiece housing, a processor disposed within the earpiece housing, the processor configured to determine characteristics of electromagnetic pulses to simulate the user's brain, and a near field magnetic inductance (NFMI) transceiver operatively connected to the processor. The may be configured to produce electromagnetic pulses capable of reaching the user's brain according to the characteristics determined by the processor. Thus, the NFMI transceiver may provide dual roles, both for NFMI communications as well as for generating electromagnetic pulses to simulate the user's brain.

According to another aspect, a set of wireless earpieces for stimulating a user's brain, wherein each wireless earpiece includes a wireless earpiece housing, a processor disposed within each earpiece housing, a near field magnetic induction (NFMI) transceiver disposed within each earpiece housing and operatively connected to the processor in the earpiece housing in which the NFMI transceiver resides, a magnetic coil mounted to each earpiece housing and operatively connected to the processor in the earpiece housing in which the magnetic coil is mounted to, and a plurality of electroencephalography (EEG) sensors mounted to each earpiece housing and operatively connected to the processor in the earpiece housing in which each of the plurality of EEG sensors is mounted to. The NFMI transceiver and the magnetic coil may be configured to produce electromagnetic pulses capable of reaching a user's brain. The plurality of EEG sensors may be configured to sense electrical signals from the users brain in response to the electromagnetic pulses.

According to another aspect, a method of stimulating a user's brain using a wireless earpiece may includes steps of receiving a request for stimulating the user's brain at the wireless earpiece from the user or a third party associated with the user, generating an electromagnetic pulse capable of reaching the user's brain by the wireless earpiece in response to receiving the request, and receiving one or more electrical signals from the user's brain at one or more electroencephalography (EEG) sensors disposed of within the wireless earpiece in response to the electromagnetic pulses and communicating the electrical signals from the user's brain to a processor disposed of within the wireless earpiece.

Various of the figures include ornamental appearance for various elements. It is to be understood that the illustrative aspects of the present invention contemplate all permutations and combinations of the various graphical elements set forth.

DETAILED DESCRIPTION

The illustrative aspects of the present invention provide a system, method, and wireless earpieces for using wireless earpieces as a tool to produce electromagnetic pulses to stimulate a user's brain. The stimulation may be utilized for medical treatments, neurological programs, prognostic prediction, enhancing memory, and so forth. In one aspect, the wireless earpieces may utilize electromagnetic signals, pulses, or programs to implement deep brain stimulation. The stimulation may be utilized to treat or monitor the symptoms or progression of Parkinson's, Huntington's, Alzheimer's, epilepsy, migraines, and any number of neurological, psychiatric, and physical conditions. The stimulation may also be utilized to treat visual-spatial memory, improve cognition, and otherwise help users. Any number of frequencies (e.g., low to ultrahigh frequencies) may be utilized to provide various cognitive benefits. In other aspects of the present invention, any number of thermal, microwave, ultrasonic, infrared, X-Ray, Gamma-ray, or other signals may also be utilized for specific treatments (e.g., cancer, tumors, comas, etc).

Figure 1:
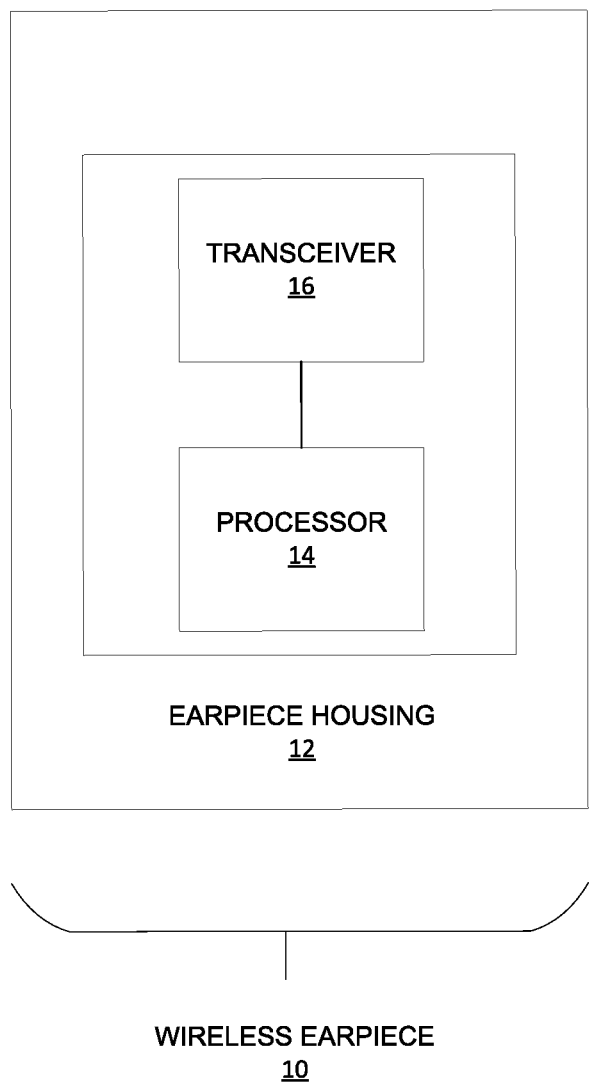
FIG. 1 illustrates a block diagram of a wireless earpiece in accordance with one aspect of the present invention.

FIG. 1 illustrates a block diagram of a wireless earpiece 10. Wireless earpiece 10 can include one wireless earpiece, a set of wireless earpieces, a wired or wireless headset, earbuds or headphones, or any other head worn device capable of providing transcranial stimulation. The wireless earpiece 10 includes a wireless earpiece housing 12, a processor 14 disposed within the earpiece housing 12, and a NFMI transceiver 16 operatively connected to the earpiece housing 12 and the processor 14. Furthermore, the NFMI transceiver 16 is configured to produce electromagnetic pulses capable of reaching a user's brain. One or more sleeves may be provided with the wireless earpiece 10 that may be fitted over a portion of the earpiece housing 12. The sleeves may come in various shapes and sizes and may be used to improve the fit of the wireless earpiece 10 within an ear of a user, improve audio transparency, improve the longevity of the wireless earpiece 10, protect the user from skin allergies, and so forth. In some aspects of the present invention, temporary adhesives or securing mechanisms (e.g., clamps, straps, extenders, etc.) may be utilized to ensure that the wireless earpiece 10 remain in the ears of a user even during the most rigorous and physical activities. For example, the wireless earpiece 10 may be utilized in wet or humid environments, during sports, or so forth. The wireless earpiece 10 may be configured to play music or audio, receive and make phone calls or other communications, activate and communicate with a digital assistant (e.g., Siri, Cortana, Alexa, smart assistant, etc.) determine ambient environmental conditions (e.g., temperature, altitude, location, speed, heading, etc.), read user biometrics (e.g., heart rate, motion, temperature, sleep, blood oxygenation, voice output, calories burned, forces experienced, etc.), and receive user input, feedback, or instructions.

The earpiece housing 12 is a structure shaped to fit substantially within an ear of the user. The earpiece housing 12 may at least partially enclose one or more of the components of the wireless earpiece 10 and may be composed of plastic, metal, polymers, non-metals, or any material or combination of materials having substantial deformation resistance in order to facilitate energy transfer if a sudden force is applied to the wireless earpiece 10. For example, if the wireless earpiece 10 is dropped by the user, the earpiece housings 12 may transfer the energy received from the surface impact throughout the entire wireless earpiece 10, minimizing damage.

In addition, the earpiece housing 12 may be capable of a degree of flexibility in order to facilitate energy absorbance if one or more forces is applied to the wireless earpiece. For example, if an object is dropped on the wireless earpiece 10, the earpiece housing 12 may bend in order to absorb the energy from the impact. The flexibility of the earpiece housing 12 should not, however, be flexible to the point where one or more components of the wireless earpiece may become dislodged or otherwise rendered non-functional due to the force of the impact. The earpiece housing 12 may waterproof enclosed components within the wireless earpiece 10.

Processor 14 is disposed within, mounted to, or integrated with the earpiece housing 12 and is operatively connected to each of the components of the wireless earpiece 10. The processor 14 may include a microprocessor, a digital signal processor, a mixed signal processor or other type of processor. The processor 14 maybe configured to implement logic for controlling one or more functions of the wireless earpiece 10. Instructions and/or data for controlling the wireless earpiece 10 may be stored on a memory of the processor 14 or associated with the processor 14.

Furthermore, the processor 14 may be programmed to execute one or more kernels, applications, programs, and/or instructions to control the wireless earpiece 10 or process information received from one or more of the components of the wireless earpiece 10. The kernels, applications, programs, and/or instructions used by the processor 14 may be stored in a memory within the processor 14 or associated therewith. For example, the processor 14 may process a request from the user to stimulate the user's temporal lobes. One or more electroencephalogram (EEG) sensors may sense electrical signals from the brain produced in response to the stimulation and communicate the sensor readings to the processor 14 for processing. The processing of the sensor readings by the processor 14 may be performed in accordance with one or more programs or applications related to evaluating or analyzing a user's memory or neurological function.

Figure 6:
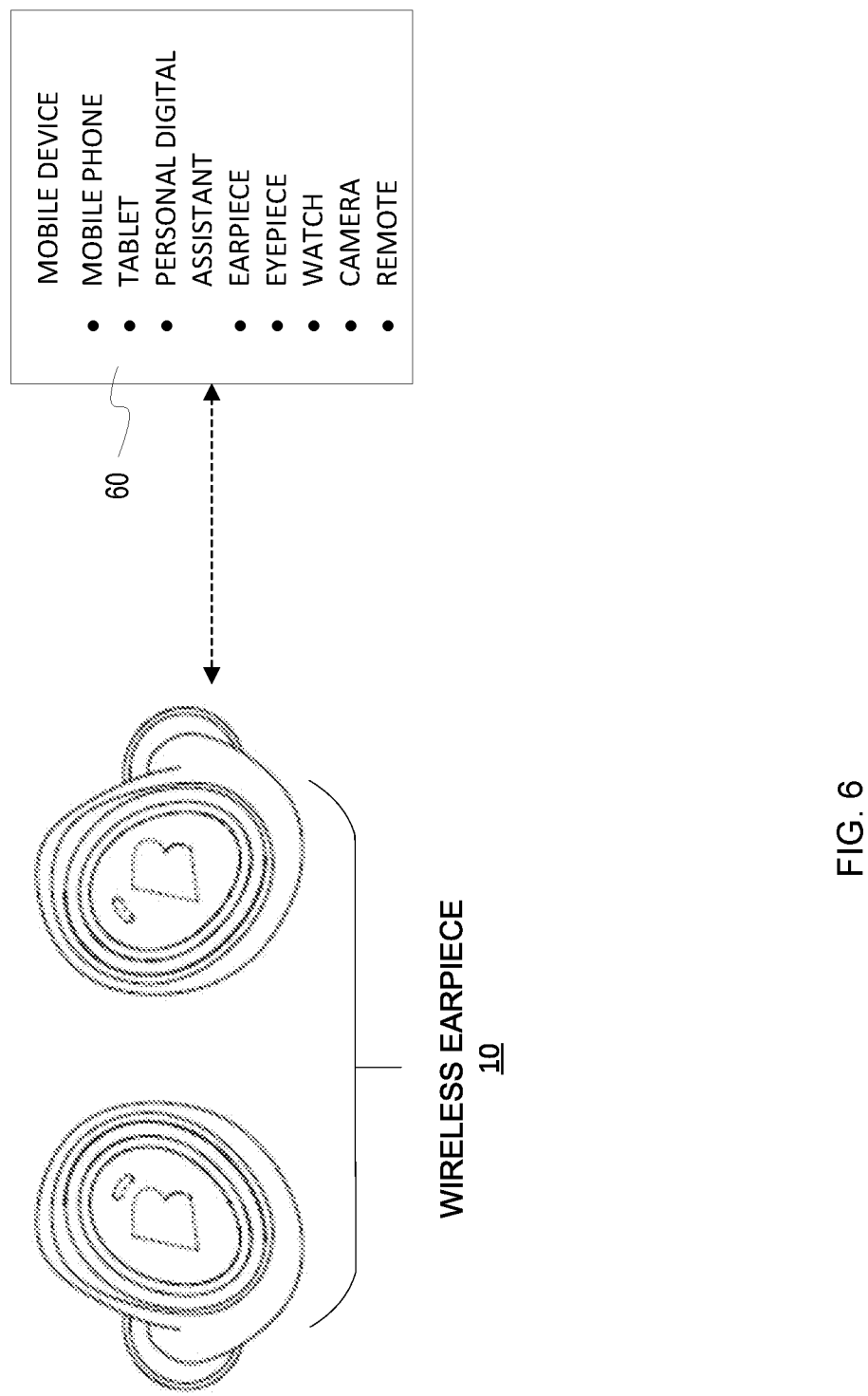
FIG. 6 illustrates a set of wireless earpieces and their relationship to a mobile device in accordance with another aspect of the present invention.

A transceiver 16 is operatively connected to the processor 14 and is disposed within, mounted to, or integrated with the earpiece housing 12. The transceiver 16 is configured to transmit electromagnetic pulses capable of reaching the user's brain. For example, the processor 14 may direct the transceiver 16 to transmit electromagnetic pulses toward the user's temporal lobes to stimulate the user's memory. The processor 14 may be programmed or otherwise configured to determine the parameters for the electromagnetic pulses which may include frequency, intensity, duration, pulse shape The transceiver 16 may be a hybrid or multi-mode transceiver and may also be configured to transmit signals to and receive signals from another electronic device such as another earpiece or the mobile device 60 as shown by FIG. 6. For example, the transceiver 16 may receive one or more signals from a mobile device or another wireless earpiece to stimulate the user's temporal lobes, and subsequently transmit a signal encoding the sensor readings or results to the same mobile device or wireless earpiece. In some embodiments, the transceiver 16 may be a near field magnetic induction transceiver (NFMI) and used both for NFMI communications and transcranial simulation.

In another aspect of the present invention, the transceiver 16 may represent a magnetic or other radio frequency transceiver. Any number of physical and wireless signals may be utilized to influence or treat the user. For example, contacts of the wireless earpiece 10 may be utilized to directly apply a stimulus and associated signal within the user's ear, to the user's head, or so forth. In other aspects, the wireless earpiece 10 may include one or more integrated, or are externally connected electrodes for attaching two other portions of the user's head.

In one aspect of the present invention, the transceiver 16 may be directionally focused on specific portions of the brain, such as the fornix. Multiple 200-Hz frequency pulses may be sent at five pulses per second for simulation. Different brain areas may be targeted with user brain activity measured, analyzed, and communicated afterwards for additional treatments, planning, and so forth. Of course, other pulse characteristics may be used including differing number of pulses, different frequencies, different durations, different pulse shapes, and other variations. In one aspect, the wireless earpiece 10 may perform transcranial magnetic stimulation of the hippocampus to enhance memory. In one aspect, the transceiver 16 may provide regular treatment sessions to the brain or specific portions of the brain. Reminders may be played to the user through the wireless earpiece 10 or through a connected wireless/computing device. As a result, the user may be able to charge and wear the wireless earpiece 10 as needed. In some aspects, the wireless earpiece 10 may be magnetically or physically connected to an external energy sources such as a battery because of the power requirements necessary to generate the electromagnetic signals over time.

Figure 2:
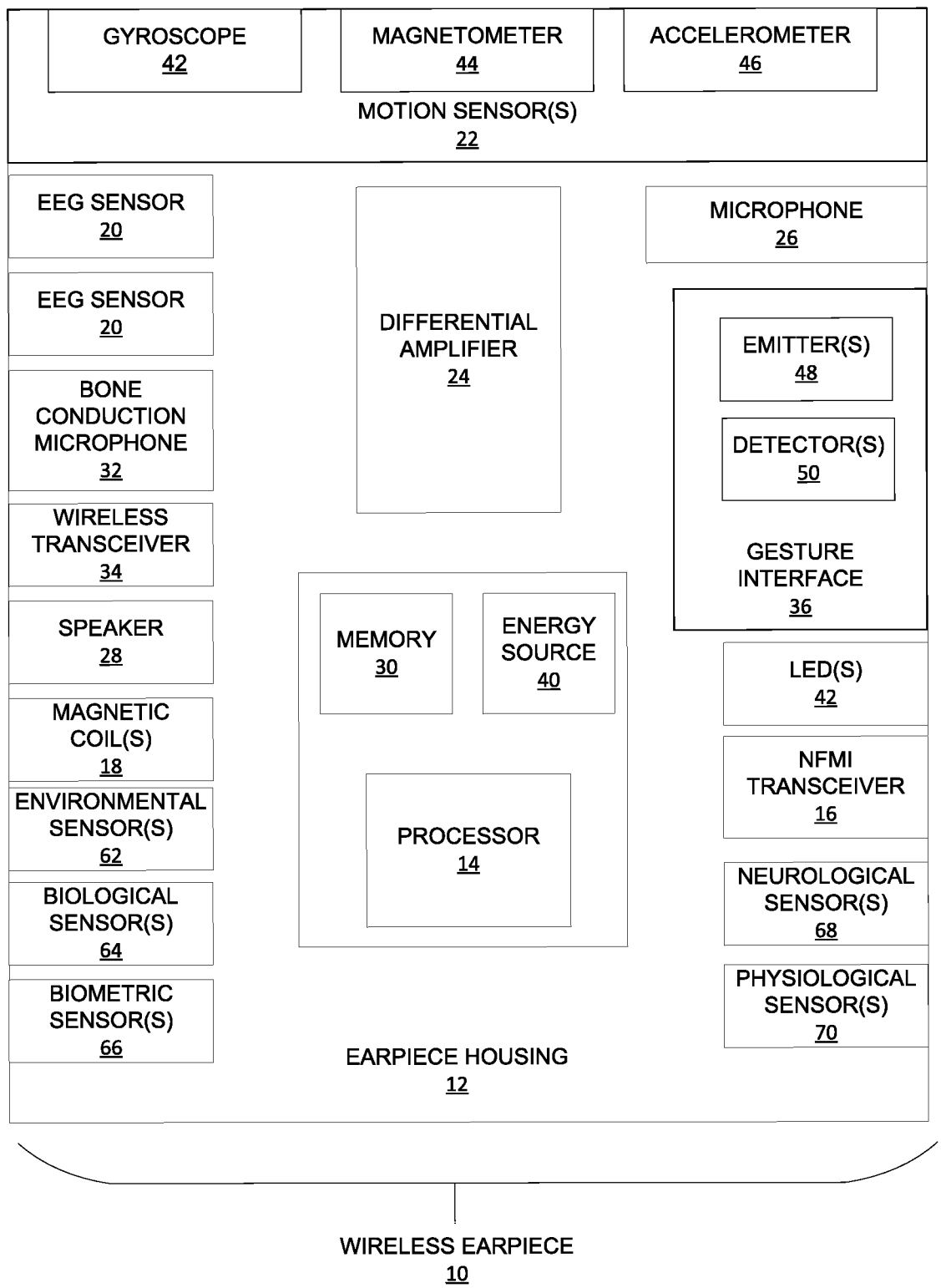
FIG. 2 illustrates a block diagram of a wireless earpiece in accordance with another aspect of the present invention.

FIG. 2 illustrates another aspect of the wireless earpiece 10. In addition to the earpiece housing 12, the processor 14, and the NFMI transceiver 16, the wireless earpiece 10 may further include a magnetic coil 18, a plurality of EEG sensors 20, one or more motion sensors 22, a differential amplifier 24, a microphone 26, a speaker 28, a memory 30, a bone conduction microphone 32, a wireless transceiver 34, a gesture interface 36, one or more LEDs 38, and an energy source 40. In some aspects of the present invention, the wireless earpiece may have additional sensors, such as environmental sensors 62, biological sensors 64, biometric sensors 66, neurological sensors 68, or physiological sensors 70.

A magnetic coil 18 may be operatively connected to the processor 14 and may be disposed within, mounted to, or integrated with the earpiece housing 12. The magnetic coil 18 may be located in an area of the wireless earpiece 10 conducive to providing electromagnetic stimulation to the user's brain and may be configured to produce continuous or intermittent electromagnetic pulses. In addition, more than one type of magnetic coil 18 may be present in the wireless earpiece 10 and each magnetic coil may have a different configuration. For example, one magnetic coil in the wireless earpiece 10 may be configured in an H formation for providing deep electromagnetic pulses, another magnetic coil may be configured in a figure-eight configuration for providing focused pulses while a third magnetic coil may be a simple round coil for providing stimulation of the user's brain near the user's ears. In addition, the physical composition of each magnetic coil 18 may include both magnetic and non-magnetic materials. In one aspect of the present invention, a number of magnetic coils 18 may be mounted onto a headband of a wireless earpiece 10, allowing transcranial stimulation from many different points along a user's skull.

A number of EEG sensors 20 may be operatively connected to the processor 14 and may be mounted to or integrated with the earpiece housing 12. Each EEG sensor 20 may be positioned at a location on the surface of the wireless earpiece 10 conducive for sensing neurological electrical activity, with at least one contact, EEG sensor, or other component acting as a ground. Multiple neurological signals of the user's brain may be obtained in order to improve informational quality. The EEG sensors 20 may receive a current from the processor 14 in order to ascertain the impedances from a voltage drop associated with each EEG sensor in order to determine which EEG sensors 20 are good candidates to sense neurological activity. In some examples, the EEG sensors 20 having lower impedances and obtain better quality signals than EEG sensors 20 having higher impedances. In addition, the portion of the EEG sensor 20 that directly interfaces with the user may be composed of conducting material to allow for better electrical readings of the user's neurological activity. EEG sensors 20 having a sufficiently low impedance may receive an activation signal from the processor 14 to receive one or more neurological signals from the user. More than one EEG sensor 20 may receive the activation signal from the processor 14. Each activated EEG sensor 20 may continuously or intermittently receive neurological signals from the user's brain until the impedance of the activated EEG sensor 20 exceeds a threshold, in which case the EEG sensor 20 may stop receiving EEG signals. Deactivated EEG sensors 20 may be reactivated by the processor 14 if the impedance of the EEG sensor falls below the threshold.

One or more motion sensors 22 may be operatively connected to the processor 14 and may be mounted to or integrated with the earpiece housing 12. The motion sensors 22 may include a MEMS gyroscope 40, a magnetometer 42, or an electronic accelerometer 44. For example, the MEMS gyroscope 40 may sense the orientation, position, or movement of the user's head relative to an initial or default position when one or more physical activities are performed. The motion sensors 22 may also include an electronic accelerometer 44, and may sense one or more accelerations related to the user's head, which may be the same physical activities used in measuring the orientation of the user's head. The readings from the MEMS gyroscope 40 and the electronic accelerometer 44 may be communicated to the processor 14, which may use the readings during execution of a transcranial stimulation program or a neurological analysis program (or other programs, processes, etc.). In addition, the processor 14 may store the readings in the memory 30 for later use. The processor may also communicate the readings to the transceiver 16 or the wireless transceiver 34. The transceiver 16 or wireless transceiver 34 may then send the sensor readings or results to a mobile device 60 or another electronic device.

In some aspects of the present invention, wireless earpiece 10 may include one or more environmental sensors 62. The environmental sensors may include external temperature sensors, altitude sensors, location sensors, heading sensors, humidity sensors, ultraviolet radiation sensors, a GPS unit or other environmental sensors. The sensor readings may be communicated to the processor. The processor 14 may store the readings in the memory 30 for later use. The processor may also communicate the readings to the wireless transceiver 34. The wireless transceiver may then send the sensor readings or results to a mobile device 60 or another electronic device.

In some aspects of the present invention the wireless earpiece 10 may include one or more biological sensors 64, biometric sensors 66 and physiological sensors 70. The biological sensors 64, biometric sensors 66, or physiological sensors 70 may include chemical sensors, pulse oximeters, a temperature sensor. Other biological or physiological sensors may include glucose sensor, alcohol sensor, bilirubin sensor, blood pressure sensor, Adenosine Triphosphate sensors, lactic acid sensor, hemoglobin sensor or other biological or physiological sensors. The sensor readings may be communicated to the processor. The processor 14 may store the readings in the memory 30 for later use. The processor may also communicate the readings to the NFMI transceiver 16 or the wireless transceiver 34. The NFMI transceiver 16 or wireless transceiver may then send the sensor readings or results to a mobile device 60 or another electronic device.

In some aspects of the present invention, the additional sensors provide a user a significant advantage. The user or a medical professional reviewing the sensor readings a broader picture of a medical condition affecting the user. For example, if the user suffers from migraines, the medical professional may analyze the EEG sensor readings, the transceiver data and or the magnetic coil data to determine when the transcranial stimulation treatment was given and the electrical signals from the user's brain in response to the electromagnetic pulses. The medical professional may also analyze the additional sensor readings at the time of treatment, prior to the treatment and after the treatment to determine a cause or a trigger of the migraine.

A differential amplifier 24 may be operatively connected to the processor 14 and each EEG sensor 20 and may be mounted to or integrated with the earpiece housing 12. The differential amplifier 24 may be configured to improve the signal quality of the neurological signals received from the EEG sensors 20. The differential amplifier 24 may remove any common mode noise present in the neurological signals received from the EEG sensors 20 and may also filter out noise received from outside electrical sources such as consumer electronic devices or appliances. The differential amplifier 24 may also filter other user or environmental noise and interference. For example, the differential amplifier 24 may remove common mode noise by subtracting the common mode gain from each signal and subsequently amplifying the difference. The common mode gain may be determined by taking the sum of each voltage received by the differential amplifier and dividing the sum by the number of signals the differential amplifier 24 received. The amplification may be anywhere from ten times to over ten thousand times, but excessive amplification may risk user safety and may risk damaging one or more components of the wireless earpiece 10. The differential amplifier 24 may also remove other noise, such as noise received from consumer electronics in the 50-60 Hertz range and artifacts due to sweating or other user movement using one or more filters. The filters may be passive high-pass filters, passive low-pass filters, quartz filters, or any other type of filter conducive to removing noise with frequencies in the hertz range. Such functionality may all be alternatively performed at the processor 14 which may, for example, be a digital signal processor.

Microphone 26 is operatively connected to the processor and may be disposed within, mounted to, or integrated with the earpiece housing 12. The microphone 26 may include one or more microphones, such as an air microphone positioned external to the body of the user when the wireless earpiece 10 is worn and an ear-bone/bone conduction microphone 32 positioned within the user's ear when the wireless earpieces 10 is worn. The microphone 26 may include components such as analog-to-digital converters, amplifiers, attenuators, filters, and/or other components necessary for the microphone to convert a sound wave into an electrical signal. The microphone 26 may be positioned on a section of the earpiece housing 12 facing away from the user's ear in order to receive a voice command or other audio input from the user or a third party. For example, the user may issue a voice command to the wireless earpiece 10 to access neurological test stored in the memory 30 via the microphone 26. In addition, voice commands and audio input received by the microphone 26 may be stored in the memory 30 for future use by one or more applications or programs stored in the memory 30.

Speaker 28 may be operatively connected to the processor 14 and may be disposed within, mounted to, or integrated with the earpiece housing 12. The speaker 28 may be positioned in an area conducive for communicating sounds to the tympanic membrane of the user's ear. Communications from the processor 14 which are transduced at the speaker 28 may include a menu for selecting one or more neurological programs, a neurological analysis, the results of a neurological test, settings information related to a neurological program, music, or other information that may be important or necessary to the user. The processor 14 may be further configured and/or programmed to generate three-dimensional stereo sound or to generate sounds at specific frequencies.

Memory 30 may be operatively connected to the processor 14 and may be disposed within, mounted to, or integrated with the earpiece housing 12. The memory 30 may be any type of non-volatile memory, which may be static and/or dynamic, allowing data storage when the wireless earpiece 10 is not powered. In some aspects of the present invention, additional volatile memories, such as random access memories, may be incorporated into the memory 30 to allow for improved functionality. The memory 30 may be configured and/or programmed to store kernels, applications, programs, instructions and/or data for either concurrent or future use and in some aspects of the present invention the memory 30 may be integrated with the processor 14 for improved functionality. The memory 30 may store sensor readings from the EEG sensors 20, motion sensors 22, or information encoded in signals received from the transceiver 34 or wireless transceiver 36 for use in programs or applications including transcranial stimulation programs for testing or improving memory, transcranial stimulation programs for alleviating depression, diagnostic programs for testing, diagnosing or monitoring neurological activity in certain areas on the user's brain, diagnostic programs related to the functionality or operation of the transceiver 16, the magnetic coils 18, the EEG sensors 20, or another program related to electromagnetic stimulation of the user's brain. In addition, memory 30 may store applications, programs, or data related to optional components of the wireless earpiece 10. In some aspects of the present invention, memory 30 may store sensor reading thresholds, user conditions, biometric sensor data, environmental sensor data, physiological sensor data, biological data, or additional neurological data.

Bone conduction microphone 32 may be operatively connected to the processor 14 and positioned on the earpiece housing 12 to make contact with a temporal bone of the user when the wireless earpiece 10 is inserted into the user's ear canal. The bone conduction microphone 32 may be configured to receive sounds and/or vibrations via the temporal bone for user's who have difficulty hearing. In addition, the bone conduction microphone 32 may be configured to help filter out sounds in order to differentiate between sounds originating from the user and sounds originating from a third party or another external location.

Wireless transceiver 34 may be operatively connected to the processor 14 and disposed within, mounted to, or integrated with the earpiece housing 12. Wireless transceiver 34 may be a Bluetooth transceiver, a WiMAX transceiver, a Wi-Fi transceiver, cellular transceiver, or another type or class of wireless transceiver that can simultaneously receive signals from electronic devices at substantial distances and meet one or more IEEE standards. The wireless transceiver 34 may be configured to receive signals from communications towers, satellites, mobile devices, desktops, laptops, watches, or other electronic devices and communicate the signals to the processor 14. The processor 14 may use the data and/or information encoded in the signals during execution of one or more programs or applications and/or store the data and/or information in the memory 30. For example, a medical professional may use an application on a mobile device 60 (see FIG. 6) to instruct the wireless earpiece 10 to test neurological activity in the user's temporal lobe. The medical professional may set the duration of pulses, amplitude, frequencies utilized, the specific area in the temporal lobe to test, and the test length using the application and subsequently transmit a signal encoding the settings to the wireless transceiver 34 of the wireless earpiece 10. The signal received by the wireless transceiver 34 may be sent to the processor 14, which may execute one or more programs or applications stored in memory 30 to instruct the transceiver 16 and/or magnetic coils 18 to transmit electromagnetic pulses in accordance with the settings desired by the medical professional. The results may be transmitted via the wireless transceiver 34 to the mobile device 60 and/or stored in the memory 30 for future use. The process may require that the devices be paired utilizing an identifier, such as a passcode, password, serial number, voice identifier, radio frequency, or so forth.

The wireless earpiece 10 may be part of a personal area network. The wireless earpieces may be utilized to control, communicate, manage, or interact with a number of other wearable devices, such as smart glasses, helmets, smart glass, watches or wrist bands, chest straps, implants, displays, clothing, or so forth. A personal area network is a network for data transmissions among devices, such as personal computing, communications, camera, vehicles, entertainment, and medical devices. The personal area network may utilize any number of wired, wireless, or hybrid configurations and may be stationary or dynamic. For example, the personal area network may utilize wireless network protocols, standards, or signals, such as INSTEON, IrDA, Wireless USB, Bluetooth, Z-Wave, ZigBee, Wi-Fi, ANT+, NFMI, or other applicable radio frequency signals.

Gesture interface 36 may be operatively connected to the processor 14 and may be mounted to or integrated with the earpiece housing 12 and may be configured to allow a user to control one or more programs or functions of the wireless earpiece 10. The gesture interface 36 may include at least one emitter 48 and at least one detector 50 to detect gestures from either the user, a third-party, an instrument, or a combination of the aforementioned components, to communicate one or more signals representing the gesture to the processor 14. The gestures that may be used with the gesture interface 36 to control the wireless earpiece 10 include, without limitation, touching, tapping, swiping, hand motions/gestures, use of an instrument, or any combination of the aforementioned gestures. Touching gestures used to control the wireless earpiece 10 may be of any duration and may include the touching of areas that are not part of the gesture interface 36. Tapping gestures used to control the wireless earpiece 10 may include any number of taps and need not be brief. Swiping gestures used to control the wireless earpiece 10 may include a single swipe, a swipe that changes direction at least once, a swipe with a time delay, a plurality of swipes, or any combination of the aforementioned. The gesture interface 36 may utilize capacitive sensors, resistive sensors, infrared sensors, optical sensors, and so forth. An instrument used to control the wireless earpiece 10 may be electronic, biochemical or mechanical, and may interface with the gesture interface 36 either physically or electromagnetically.

LEDs 38 may be operatively connected to the processor 14 and may be mounted to or integrated with the earpiece housing 12. The LEDs 38 may be semiconductor-based light sources and may include displays, touch sensors, and/or other interactive interface components. In addition, the LEDs 38 may be configured to provide information concerning the wireless earpiece 10. For example, the processor 14 may communicate a signal encoding information related to the current time, the energy level of the wireless earpiece 10, the status of another operation of the wireless earpiece 10, or another wireless earpiece program or function to the LEDs 38. If the signal concerns the energy level of the wireless earpiece 10, the LEDs 38 may decode the signal as a colored light. For example, a green light may represent a substantial level of battery life, a yellow light may represent an intermediate level of battery life, a red light may represent a limited amount of battery life, and a blinking red light may represent a critical level of battery life requiring immediate recharging. In addition, the battery life may be represented by the LEDs 38 as a percentage of battery life remaining or may be represented by an energy bar having one or more LEDs, wherein the number of illuminated LEDs represents the amount of battery life remaining in the wireless earpiece. The LEDs 38 may be located in any area on the wireless earpiece 10 suitable for viewing by the user or a third party and may also consist of as few as one diode which may be provided in combination with a light guide. In addition, the LEDs 38 need not have a minimum luminescence. The LEDs 38 may work with the speaker 28 to visually and audibly present information to the user.

Energy source 40 is operatively connected to all of the components within the wireless earpiece 10. The energy source 40 may provide enough power to operate the wireless earpiece 10 for a reasonable duration of time. The energy source 40 may be of any type suitable for powering the wireless earpiece 10, such as batteries, solar cells, fuel cells, ultra-capacitors, piezo electric generators, thermal generators, and so forth. However, the energy source 40 need not be present in the wireless earpiece 10. Alternative battery-less power sources, such as sensors configured to receive energy from radio waves (all of which are operatively connected to one or more wireless earpieces) may be used to power the wireless earpiece 10 in lieu of an energy source 40.

Figure 3:
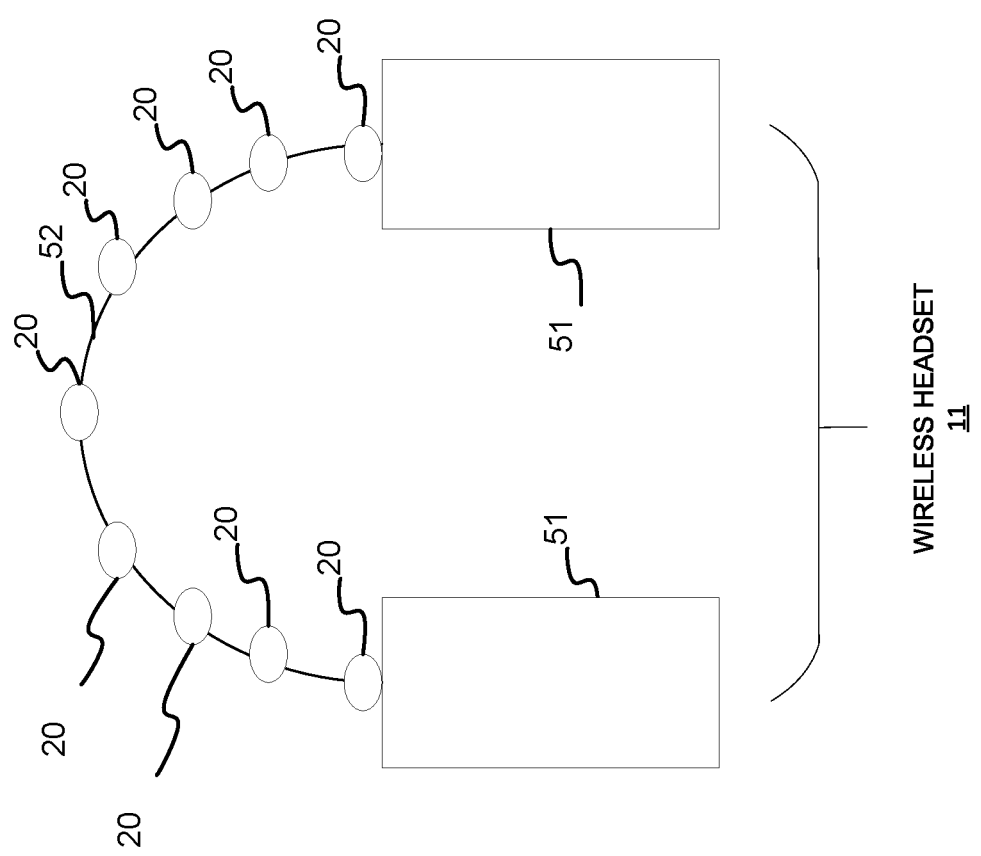
FIG. 3 illustrates a wireless headset in accordance with another aspect of the present invention.

FIG. 3 illustrates another aspect of a wireless earpiece as a wireless headset 10. The wireless headset 11 may include the components outlined in FIGS. 1 and 2 including a transceiver 16 configured to generate electromagnetic pulses capable of reaching a user's brain (as shown in FIG. 1). In addition, the wireless headset 11 may include a pair of earpads 51 connected to opposite ends of a headband 52 configured to be worn on a user's head. The earpads 51 may fit around, on, or within a user's ears and may partially or completely enclose the outer ear canals of the user.

In one aspect of the present invention, the processor 14 and transceiver (not shown) may be positioned anywhere within the wireless headset 11. In addition, one or more magnetic coils (not shown) may be positioned along the headband 52 and/or the earpads 51 to generate electromagnetic pulses capable of reaching the user's brain. Each magnetic coil may differ by geometry, chemical composition, and/or pulse generation profile. For example, conically-shaped magnetic coils composed of ferrous materials may be mounted to the headband for stimulating certain portions of the user's frontal or parietal lobes, magnetically inert round coils may be mounted to or integrated with each earpad 51 to stimulate a user's temporal lobes, and H-shaped coils may be placed at various locations on the wireless headset 11 for deeper stimulation of the brain. Other types of coils such as butterfly and/or four-leaf coils may also be present in the wireless headset 11. The magnetic coils 18 may be flexible and conform to the shape and size of the user's head. In one aspect of the present invention, the magnetic coils may form a net, array, or lattice for communicating signals and receiving signals from the user. In another aspect, portions of the magnetic coils may be utilized as an antenna or wave guide for sending signals and other portions of the magnetic coils may be utilized to receive electrical signals (e.g., EEG signals communicated to EEG sensors 20 or other components of the wireless headset 11).

One or more EEG sensors 20 may also be positioned along the headband 52 and/or the earpads 51 to sense electrical activity from the brain resulting from the electromagnetic pulses of the NFMI transceiver and/or the magnetic coils. The readings from the EEG sensors 20 may be used with various neurological programs and/or applications within the wireless headset 11. For example, a program for diagnosing brain activity in stroke victims may stimulate an area of the user's brain affected by a stroke using one or more magnetic coils and subsequently use the resulting EEG sensor readings to generate a series of values which may be used by a doctor or another medical professional to diagnose the amount of damage in the affected area. The values may be provided using one or more LEDs present on the wireless headset 11 or may be encoded in a signal and transmitted by the transceiver 16 to a mobile device or another computing device capable of interpreting the encoded signal.

Figure 4:
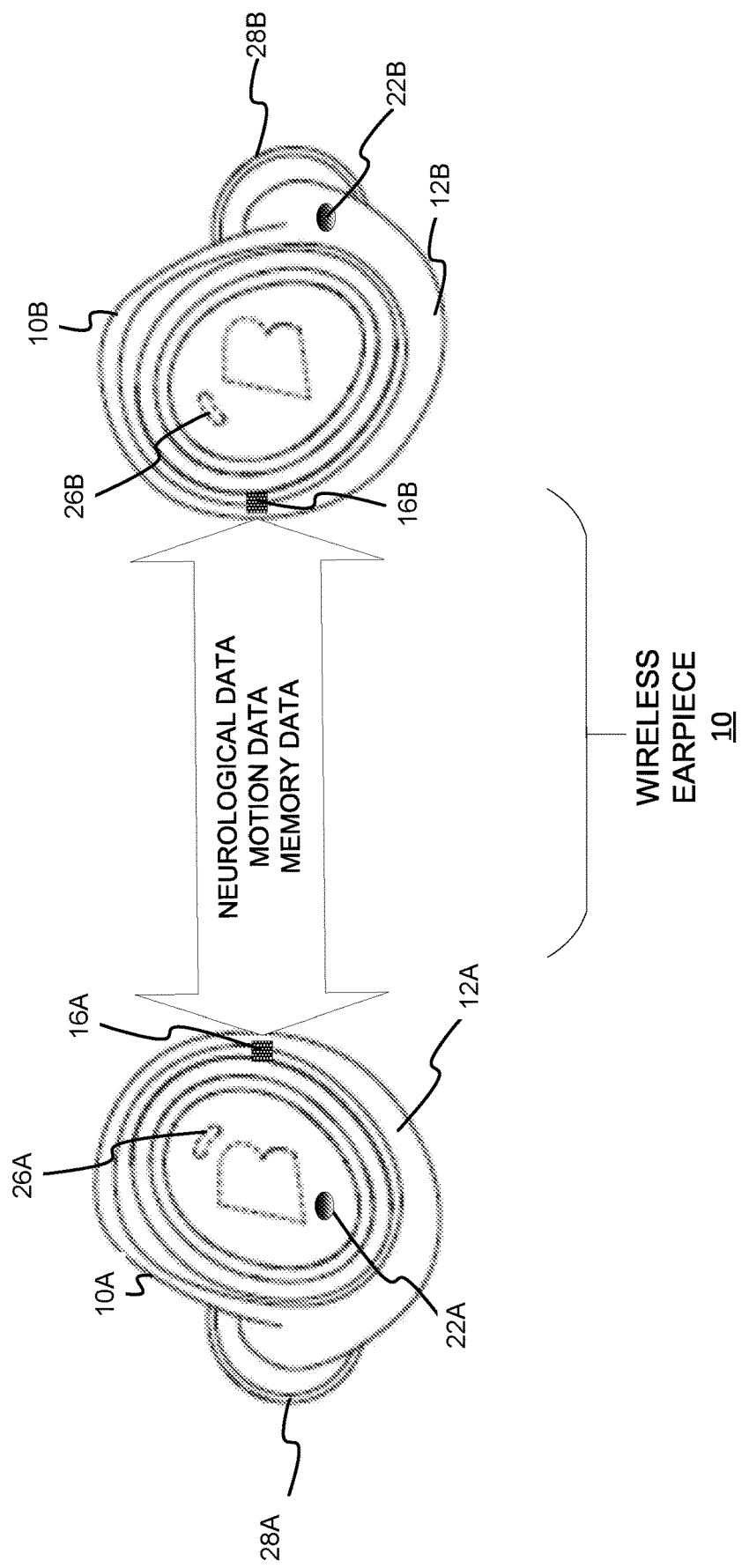
FIG. 4 illustrates a set of wireless earpieces in accordance with another aspect of the present invention.

FIG. 4 illustrates a set of wireless earpieces 10 which includes a left wireless earpiece 10A and a right wireless earpiece 10B. The left wireless earpiece 10A has a left earpiece housing 12A. The right wireless earpiece 10B has a right earpiece housing 12B. The left wireless earpiece 10A and the right wireless earpiece 10B may be configured to fit on, over, or within a user's external auditory canal and may be configured to substantially minimize or eliminate external sound capable of reaching the user's tympanic membranes.

The earpiece housings 12A and 12B may be composed of any material with substantial deformation resistance and may also be configured to be soundproof or waterproof. Transceivers 16A and 16B are shown. In some illustrative aspects of the present invention, the transceivers 16A, 16B may be disposed within earpiece housings 12A, 12B. Transceivers 16A and 16B may be configured to generate one or more electromagnetic pulses capable of reaching a user's brain when worn and each transceiver 16A, 16B may transmit and/or receive signals encoding information related to information concerning a user's mental or neurological state. For example, the transceivers may exchange information related to EEG signals for use in memory, neurological, or other mental programs. In addition, neurological or memory related programs and applications may also be shared between the left wireless earpiece 10A and the right wireless earpiece 10B via the transceivers 16A, 16B such as when the transceivers are NFMI transceivers.

Figure 5:
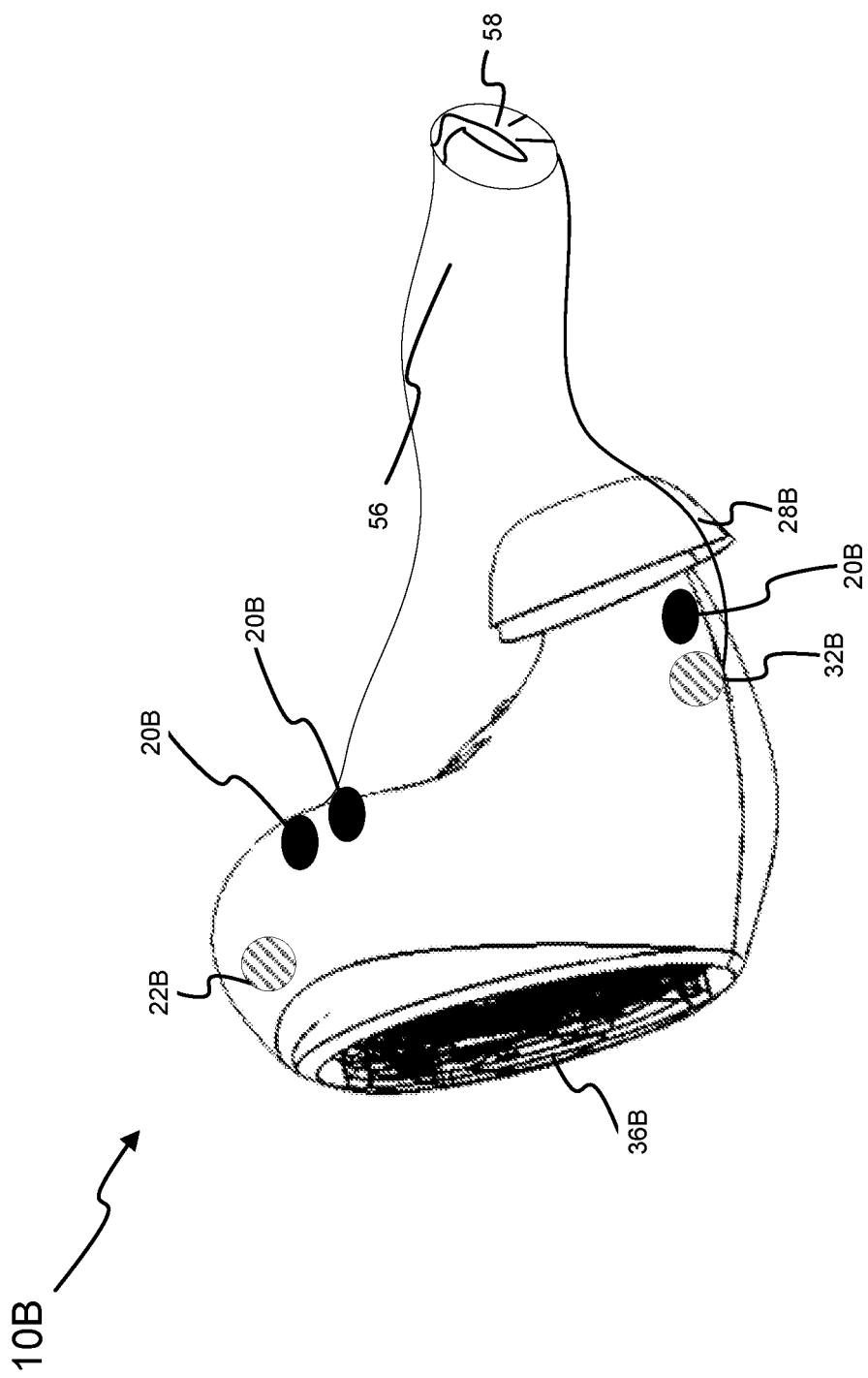
FIG. 5 illustrates a right wireless earpiece and its relationship to a user's ear in accordance with another aspect of the present invention.

Motion sensors 22A and 22B are also shown. Motion sensors 22A and 22B may be configured to sense any body movements performed by the user for use in a memory or neurological diagnostic application. Microphones 26A and 26B are also shown. The microphones 26A and 26B may be located anywhere on the left wireless earpiece 10A and the right wireless earpiece 10B respectively and each microphone may be positioned to receive one or more sounds or voice commands from the user, one or more sounds from a third party, or one or more ambient sounds from an object worn or carried by the user or the outside environment, whether natural or artificial. A speaker 28A is shown on the left wireless earpiece 10A and a speaker 28B is shown on the right wireless earpiece 10B. Speakers 28A and 28B may be positioned proximate to the user's tympanic membranes FIG. 5 illustrates a side view of the right wireless earpiece 10B and its relationship to a user's ear. The right wireless earpiece 10B may be configured to both minimize the amount of external sound reaching the user's external auditory canal 56 and to facilitate the transmission of communicated sounds from the speaker 28B to a user's tympanic membrane 58. The right wireless earpiece 10B may also be configured to be of any size necessary to comfortably fit within the user's external auditory canal 56.

A plurality of EEG sensors 20 may be positioned proximate to an inner surface of the user's external auditory canal and may be configured to receive one or more electrical signals from the user's brain. A motion sensor 22B, which may include an MEMS gyroscope 42, an accelerometer 46, or a magnetometer 44, may be positioned on the right wireless earpiece 10B to sense one or more body movements. In addition, a bone conduction microphone 32B may be positioned near the temporal bone of the user's skull in order to produce sound vibrations for people who have difficulty speaking loudly. The bone conduction microphone 32B may also sense sounds before the sounds reach the external or over-air microphones 26B (see FIG. 4) in order to differentiate between sounds from the user and ambient sounds. The gesture interface 36B may provide for gesture control by the user or a third party such as by tapping or swiping across the gesture interface 36B, tapping or swiping across another portion of the right wireless earpiece 50B, providing a gesture not involving the touching of the gesture interface 36B or another part of the right wireless earpiece 50B, or through the use of an instrument configured to interact with the gesture interface 36B. The user may use the gesture interface 36B to select a memory or neurological diagnostic program or to control another function of the right wireless earpiece 50B.

FIG. 6 illustrates a set of wireless earpieces 10 and their relationship to a mobile device 60. The mobile device 60 may be a mobile phone, a tablet, a gaming device, a virtual reality/augmented reality system, a laptop computer, a watch, a PDA, a remote, an eyepiece, a wireless earpiece, or any electronic device not requiring a fixed location. The user may use a software application on the mobile device 60 to select a memory or neurological program or diagnostic application to use with one of the wireless earpieces 60. The selection may be communicated to the wireless earpiece 10 via a transceiver of the mobile device 60. In addition, the user may use the mobile device 60 to download memory tests, neurological applications, and/or neurological diagnostic applications to the wireless earpiece 10 where the software may be used directly. Other programs may be downloaded to the wireless earpiece 10 using the mobile device 60 as well. The mobile device 60 may also download results related to memory or neurological tests performed by the user from the wireless earpiece 10 for analysis. For example, a medical professional may wish to see the results of a neurological test in making a diagnosis related to dementia or Alzheimer's disease. The wireless earpiece 10 may also process the sensor readings, or electrical signals into a format that is more easily communicated to the mobile device 60 which may include packetization, frame generation, signal processing and preparation, data encryption, digital-to-analog conversion, data compression, modulation, coding, and so forth.

Figure 7:
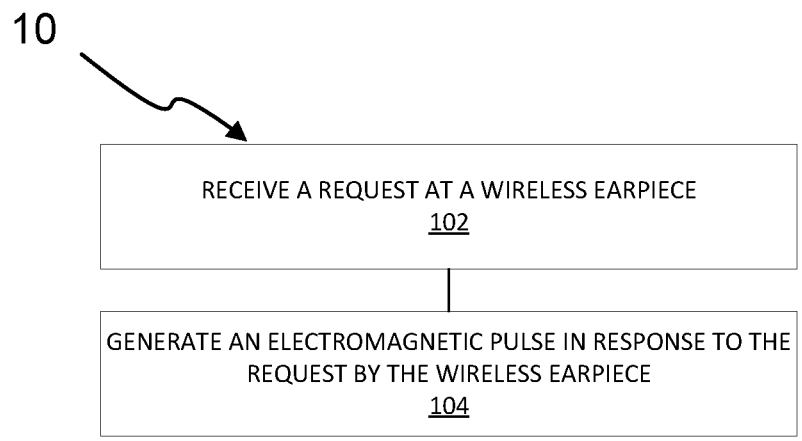
FIG. 7 illustrates a flowchart of a method of stimulating a user's brain using a wireless earpiece in accordance with another aspect of the present invention.

FIG. 7 illustrates a flowchart of a method of stimulating a user's brain using a wireless earpiece 10. First, in step 102, the wireless earpiece 10 receives a request to stimulate the user's brain. The request may be performed using (1) a voice command received by a microphone 26 and/or bone conduction microphone 32 or (2) a gesture sensed by a gesture interface 36. For example, the gesture may be associated with a command that instructs the speaker, vibration components, tactile interface, lights, or other output components to communicate a menu having one or more choices to the user. The choices may include programs such as transcranial stimulation programs for testing or improving memory, transcranial stimulation programs for alleviating depression, diagnostic programs for testing and monitoring neurological activity in certain areas on the user's brain, diagnostic programs related to the functionality or operation of the transceiver 16, the magnetic coils 18, the EEG sensors 20, or another program related to electromagnetic stimulation of the user's brain. The choices may be selected using another voice command or an additional gesture if making a selection using the gesture interface 36. In step 104, an electromagnetic pulse is generated in response to the request by the wireless earpiece. The electromagnetic pulse may be generated directly in response to a voice command or gesture or the electromagnetic pulse may be generated in accordance with one or more programs selected by the user or a third party. In one aspect of the present invention, the electromagnetic pulse may represent a single pulse, series of pulses, sequence of pulses, programs, or other combination of signals and stimuli capable of being communicated by the wireless earpiece. For example, electromagnetic pulses of a first frequency may begin from an extremely low amplitude to a higher amplitude as a form of treatment. Additional frequencies may also be similarly utilized. In another example, combinations of frequencies and amplitudes may be utilized for the treatment or stimulation of the user's brain. In one aspect of the present invention, the electromagnetic pulses may be controlled by a program uploaded or sent to the wireless earpiece by a medical professional associated with the user. As noted, the electromagnetic pulse may represent any single pulse, program, or series of pulses (and other stimuli) utilized by the wireless earpiece.

Figure 8:
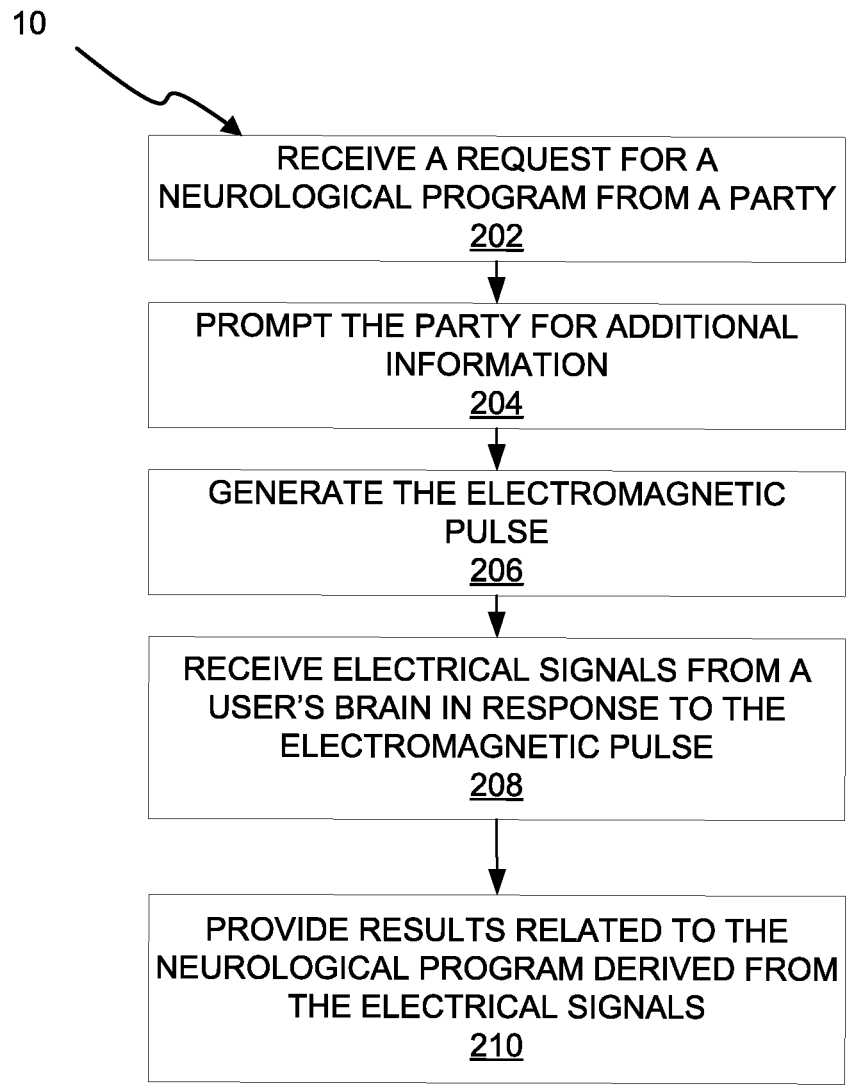
FIG. 8 illustrates a flowchart of another aspect of a method of stimulating a user's brain using a wireless earpiece in accordance with another aspect of the present invention.

FIG. 8 illustrates a flowchart of a another aspect of stimulating a user's brain using the wireless earpiece 10. Initially, in step 202, the wireless earpiece receives a request for a neurological program. The request may be performed using (1) a voice command received by a microphone and/or bone conduction microphone or (2) a gesture sensed by a gesture interface as previously noted (i.e., step 102 of FIG. 1). The user may select one of the choices using another voice command or an additional gesture if making a selection using the gesture interface.

In step 204, the wireless earpiece 10 prompts a party for additional information. The additional information may be provided by the user or a third party such as a doctor or medical professional associated with the user. The additional information may relate to the user's age, health, previous neurological stimulations, or other criteria needed by the program.

In step 206 an electromagnetic pulse is generated. The electromagnetic pulse may be generated by a transceiver and/or one or more magnetic coils with differing compositions, geometries, and/or pulse generation profiles. The electromagnetic pulse may be sent through one or more antennas, focus components, waveguides, or so forth. In addition, the electromagnetic pulse may be generated in accordance with instructions within a program or in response to one or more additional inputs from the user, one or more third parties associated with the user, or a component of the wireless earpiece. The electromagnetic pulse may reach anywhere from a few millimeters to many centimeters into the user's brain.

In step 208 a plurality of EEG sensors 20 receives electrical signals from the user's brain in response to the electromagnetic pulse. A differential amplifier may be used to remove common mode gains and filter extraneous electrical signals from the wireless earpiece or other electrical objects from the electrical signals of the user's brain. The received signals may be processed in any number of ways including neurological analysis. During step 208, the received signals and measurements may be analyzed by the wireless earpiece 10 or sent for analysis or processing by an externally linked device.

In step 210 results derived from the electrical signals are provided to a user or a third party associated with the user. The results may be provided by the wireless earpiece 10 to allow the user or a third party to make a diagnosis, which may be at least partially performed by the wireless earpiece 10. For example, the EEG sensor readings may be compared to EEG sensor readings from a previous session or to a model corresponding to healthy EEG sensor readings, with the results provided to the user and/or third party via the wireless earpiece to allow the user or third party to make the diagnosis. In addition, the EEG sensor readings may be communicated without analysis by the neurological program to the user and/or third party. The user or third party may then make a diagnosis directly using the EEG sensor readings. For example, the results may be communicated from the wireless earpiece 10 to a mobile device 60 or a computer for analysis or further relaying to a designated location, user, or device. In some aspects of the invention, additional sensor readings, such as environmental sensor readings from the environmental sensors 63, biological sensor readings from the biological sensors 64, biometric readings from the biometric sensors 66, additional neurological sensor readings from the neurological sensors 68, physiological sensor readings from the physiological sensors 78, or a combination thereof may be communicated from the wireless earpiece 10 to a mobile device 60 or a computer for analysis or further relaying to designated location user, or device. The wireless earpiece 10 may also process the sensor measurements into a format that is more easily communicated to the mobile device 60 which may include packetization, frame generation, signal processing and preparation, data encryption, digital-to-analog conversion, data compression, modulation, coding, and so forth.

The illustrative aspects of the present invention are not to be limited to the particular aspects of the present invention and examples described herein. In particular, the illustrative aspects of the present invention contemplate numerous variations in the type of ways in which different aspects of the present invention may be applied to wireless earpieces. The foregoing description has been presented for purposes of illustration and description. It is not intended to be an exhaustive list or limit any of the disclosure to the precise forms disclosed. It is contemplated that other alternatives or exemplary aspects are considered included in the disclosure. The description is merely examples of aspects, processes or methods of the invention. It is understood that any other modifications, substitutions, and/or additions may be made, which are within the intended spirit and scope of the disclosure. For the foregoing, it can be seen that the disclosure accomplishes at least all of the intended objectives. The illustrative aspects of the present invention including various description and examples are meant to be applied across the various figures and illustrative aspects of the present invention regardless of assertions, classifications, and so forth.

The previous detailed description is of a small number of illustrative aspects for implementing the invention and is not intended to be limiting in scope. The following claims set forth a number of the illustrative aspects disclosed with greater particularity.

What is claimed is:

1. A wireless earpiece for stimulating a user's brain comprising:
   a wireless earpiece housing;
   a processor disposed within the earpiece housing, the processor configured to determine characteristics of electromagnetic pulses to stimulate the user's brain;
   a near field magnetic inductance (NFMI) transceiver operatively connected to the processor; and
   wherein the NFMI transceiver is both (1) configured to produce electromagnetic pulses capable of reaching the user's brain according to the characteristics determined by the processor and (2) configured to wirelessly communicate with another wireless earpiece.

2. The wireless earpiece of claim 1, further comprising a memory operatively connected to the earpiece housing and processor.

3. The wireless earpiece of claim 2, wherein a neurological program is stored on the memory.

4. The wireless earpiece of claim 3, wherein the neurological program comprises a set of instructions for diagnosing a user's memory.

5. The wireless earpiece of claim 1, further comprising a magnetic coil configured to produce electromagnetic pulses capable of reaching the user's brain operatively connected to the processor.

6. The wireless earpiece of claim 1, further comprising a plurality of electroencephalography (EEG) sensors configured to sense electrical signals from the user's brain in response to the electromagnetic pulses operatively connected to the processor for sensing.

7. The wireless earpiece of claim 6, further comprising a differential amplifier operatively connected to the processor and each of the plurality of EEG sensors.

8. The wireless earpiece of claim 1, wherein the wireless earpiece is within a headset.

9. A set of wireless earpieces for stimulating a user's brain, wherein each wireless earpiece comprises:
   a wireless earpiece housing;
   a processor disposed within each earpiece housing;

a near field magnetic induction (NFMI) transceiver disposed within each earpiece housing and operatively connected to the processor in the earpiece housing in which the NFMI transceiver resides;

a magnetic coil mounted to each earpiece housing and operatively connected to the processor in the earpiece housing in which the magnetic coil is mounted to: a plurality of electroencephalography (EEG) sensors mounted to each earpiece housing and operatively connected to the processor in the earpiece housing in which each of the plurality of EEG sensors is mounted to;

wherein the NFMI transceiver and the magnetic coil are configured to produce electromagnetic pulses capable of reaching a user's brain;

wherein the NFMI transceiver is further configured to communicate with another wireless earpiece; and wherein the plurality of EEG sensors are configured to sense electrical signals from the users brain in response to the electromagnetic pulses.

10. The set of wireless earpieces of claim 9, wherein each of the wireless earpieces further comprises a wireless radio transceiver disposed within each earpiece housing and operatively connected to the processor in the earpiece housing in which the wireless radio transceiver resides.

11. The set of wireless earpieces of claim 9, wherein each wireless earpiece further comprises a memory disposed within each earpiece housing and operatively connected to the processor in the earpiece housing in which the memory resides and wherein each memory includes a neurological program.

12. The set of wireless earpieces of claim 9, further comprising a differential amplifier disposed within each earpiece housing and operatively connected to the processor in the earpiece housing in which the differential amplifier resides, and wherein each differential amplifier is configured to remove common mode gains from the electrical signals from the brain of the user.

13. The set of wireless earpieces of claim 12, wherein each differential amplifier is further configured to filter out noise caused by one or more electronic devices from the electrical signals from the user's brain.

14. A method of stimulating a user's brain using a wireless earpiece comprising:

receiving a request for stimulating the user's brain at the wireless earpiece from the user or a third party associated with the user; and generating an electromagnetic pulse capable of reaching the user's brain by the wireless earpiece in response to receiving the request;

wherein the electromagnetic pulse is generated by a near field magnetic inductance (NFMI) transceiver disposed within the wireless earpiece;

wherein the NFMI transceiver is further configured to wireless communicate with another wireless earpiece;

receiving one or more electrical signals from the user's brain at one or more electroencephalography (EEG) sensors disposed of within the wireless earpiece in response to the electromagnetic pulses and communicating the electrical signals from the user's brain to a processor disposed of within the wireless earpiece.

15. The method of claim 14 further comprising the wireless earpiece prompting a party for additional information if the request is a request to use a neurological program stored in a memory disposed of within the wireless earpiece.

16. The method of claim 15, wherein the party is the user or a third party associated with the user.

17. The method of claim 14, further comprising:

analyzing the one or more electrical signals from the user's brain to generate results related to the electrical signals from the user's brain by the processor disposed of within the wireless earpiece; and providing results related to the electrical signals from the user's brain to the user or a third party associated with the user by sending the results from a transceiver disposed of within the wireless earpiece to an externally linked device.

18. The method of claim 17, wherein the results comprise neurological analysis of the electrical signals form from the user's brain.

* * * * *